United States Patent
Hart et al.

(10) Patent No.: US 10,258,566 B2
(45) Date of Patent: *Apr. 16, 2019

(54) COMPOSITIONS AND METHODS FOR TREATING BONE

(75) Inventors: Charles E. Hart, Brentwood, TN (US); Jeffrey O. Hollinger, Gibsonia, PA (US); Samuel E. Lynch, Franklin, TN (US)

(73) Assignee: BIOMIMETIC THERAPEUTICS, LLC, Franklin, TN (US)

( * ) Notice: Subject to any disclaimer, the term of this patent is extended or adjusted under 35 U.S.C. 154(b) by 573 days.

This patent is subject to a terminal disclaimer.

(21) Appl. No.: 12/819,093

(22) Filed: Jun. 18, 2010

(65) Prior Publication Data

US 2011/0117018 A1   May 19, 2011

Related U.S. Application Data

(63) Continuation of application No. 11/704,685, filed on Feb. 9, 2007, now Pat. No. 7,799,754, which is a continuation-in-part of application No. 11/159,533, filed on Jun. 23, 2005, now Pat. No. 7,473,678, which is a continuation-in-part of application No. 10/965,319, filed on Oct. 14, 2004, now abandoned.

(60) Provisional application No. 60/771,826, filed on Feb. 9, 2006, provisional application No. 60/817,988, filed on Jun. 30, 2006, provisional application No. 60/859,809, filed on Nov. 17, 2006.

(51) Int. Cl.

| | | |
|---|---|---|
| *A61K 38/18* | (2006.01) |
| *A61K 47/02* | (2006.01) |
| *A61K 9/14* | (2006.01) |
| *A61L 27/12* | (2006.01) |
| *A61L 27/24* | (2006.01) |
| *A61L 27/46* | (2006.01) |
| *A61K 49/04* | (2006.01) |
| *A61P 19/08* | (2006.01) |
| *A61K 9/00* | (2006.01) |
| *A61L 27/22* | (2006.01) |
| *A61L 27/42* | (2006.01) |

(52) U.S. Cl.
CPC ........ *A61K 9/0024* (2013.01); *A61K 38/1858* (2013.01); *A61K 47/02* (2013.01); *A61L 27/12* (2013.01); *A61L 27/227* (2013.01); *A61L 27/24* (2013.01); *A61L 27/425* (2013.01); *A61L 27/46* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,943,072 A | 3/1976 | Thomson et al. |
| 4,795,467 A | 1/1989 | Piez et al. |
| 4,845,075 A | 7/1989 | Murray et al. |
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A * | 9/1992 | Rutherford ............ 424/484 |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,338,772 A * | 8/1994 | Bauer et al. ............ 523/115 |
| 5,376,636 A | 12/1994 | Rutherford et al. |
| 5,457,093 A | 10/1995 | Cini et al. |
| 5,460,962 A | 10/1995 | Kemp |
| 5,516,896 A | 5/1996 | Murray et al. |

(Continued)

FOREIGN PATENT DOCUMENTS

| | | |
|---|---|---|
| EP | 0 289 584 B1 | 11/1988 |
| EP | 0 479 799 B1 | 4/1992 |

(Continued)

OTHER PUBLICATIONS

Paul et al., J. Mater. Sci. Mater. Med., 1999, vol. 10(7):383-388.*
Nevins et al., J. Periodontol., Sep. 2003; 74(9):1282-1292.*
Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2Fwww%2E7ware% . . . >, last visited on Feb. 24, 2010, 2 pages.
Adalberto et al. "Periodontal Regeneration," *J. Periodontal*, 2005, 76(9):1601-1622.

(Continued)

*Primary Examiner* — Xiaozhen Xie
(74) *Attorney, Agent, or Firm* — Patterson Intellectual Property Law, PC; Hilary Dorr Lang

(57) ABSTRACT

The present invention relates to compositions, methods and kits for the treatment of bone particularly impaired or damaged bone.

17 Claims, 7 Drawing Sheets

(56) References Cited

U.S. PATENT DOCUMENTS

| | | |
|---|---|---|
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,783,217 A | 7/1998 | Lee et al. |
| 5,804,176 A | 9/1998 | Grotendorst |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,030,636 A | 2/2000 | Randolph et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 7,799,754 B2 | 9/2010 | Hart et al. |
| 7,943,573 B2 | 5/2011 | Lynch et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1* | 3/2003 | Dalal et al. .................. 424/602 |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1* | 1/2004 | King et al. .................. 623/23.51 |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0084602 A1 | 4/2006 | Lynch |
| 2006/0148024 A1 | 7/2006 | Savage |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |

(56) References Cited

U.S. PATENT DOCUMENTS

| | | |
|---|---|---|
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0207185 A1 | 9/2007 | Hart et al. |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0259814 A1 | 11/2007 | Lynch |
| 2007/0260326 A1 | 11/2007 | Williams et al. |
| 2007/0282455 A1 | 12/2007 | Luginbuehl et al. |
| 2008/0027470 A1 | 1/2008 | Hart et al. |
| 2008/0193424 A1 | 8/2008 | McKale et al. |
| 2008/0200372 A1 | 8/2008 | Ghosh |
| 2009/0054339 A1 | 2/2009 | Marshall et al. |
| 2009/0074753 A1 | 3/2009 | Lynch |
| 2009/0092674 A1 | 4/2009 | Ingram et al. |
| 2009/0130173 A1 | 5/2009 | Behnam et al. |
| 2009/0232890 A1 | 9/2009 | Lynch et al. |
| 2010/0136085 A1 | 6/2010 | Hart et al. |
| 2010/0151025 A1 | 6/2010 | Lynch et al. |
| 2010/0174368 A1 | 7/2010 | Lynch et al. |
| 2010/0183515 A1 | 7/2010 | Hart et al. |
| 2010/0196347 A1 | 8/2010 | Kery et al. |
| 2010/0247651 A1 | 9/2010 | Kestler et al. |

FOREIGN PATENT DOCUMENTS

| | | |
|---|---|---|
| EP | 0530804 A1 | 3/1993 |
| EP | 0530804 B1 | 3/1993 |
| EP | 0 741 785 B1 | 11/1996 |
| EP | 0 741 785 B2 | 11/1996 |
| EP | 0 896 825 A1 | 2/1999 |
| EP | 0 896 825 B1 | 2/1999 |
| EP | 0 994 694 B1 | 4/2000 |
| EP | 1 025 871 A1 | 8/2000 |
| EP | 1 100 488 B1 | 5/2001 |
| EP | 1 146 897 B1 | 10/2001 |
| EP | 1 234 552 A1 | 8/2002 |
| EP | 1 234 552 B1 | 8/2002 |
| EP | 1 242 129 B1 | 9/2002 |
| EP | 1 374 857 A1 | 1/2004 |
| EP | 1 410 811 A1 | 4/2004 |
| EP | 1 410 811 B1 | 4/2004 |
| EP | 1 464 307 A1 | 10/2004 |
| EP | 1 464 307 B1 | 10/2004 |
| EP | 1 561 481 A2 | 8/2005 |
| EP | 1 561 481 A3 | 8/2005 |
| EP | 1 563 846 A1 | 8/2005 |
| EP | 1 681 087 A2 | 7/2006 |
| EP | 1 681 087 A3 | 7/2006 |
| EP | 1 712 244 A1 | 10/2006 |
| EP | 1 719 531 A2 | 11/2006 |
| EP | 1 719 532 A2 | 11/2006 |
| GB | 2 367 497 A | 4/2002 |
| JP | 7-250688 A | 10/1995 |
| JP | 2003-265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/16035 A3 | 6/1995 |
| WO | WO-95/18856 A1 | 7/1995 |
| WO | WO-95/20967 A1 | 8/1995 |
| WO | WO-95/28124 A2 | 10/1995 |
| WO | WO-95/28124 A3 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-96/17924 A3 | 6/1996 |
| WO | WO-97/13857 A1 | 4/1997 |
| WO | WO-98/00183 A2 | 1/1998 |
| WO | WO-98/00183 A3 | 1/1998 |
| WO | WO-98/40113 A1 | 9/1998 |
| WO | WO-98/41246 A2 | 9/1998 |
| WO | WO-98/41246 A3 | 9/1998 |
| WO | WO-98/51354 A2 | 11/1998 |
| WO | WO-98/51354 A3 | 11/1998 |
| WO | WO-99/30726 A1 | 6/1999 |
| WO | WO-99/38543 A2 | 8/1999 |
| WO | WO-99/38543 A3 | 8/1999 |
| WO | WO-99/67289 A1 | 12/1999 |
| WO | WO-00/04940 A1 | 2/2000 |
| WO | WO-01/32197 A2 | 5/2001 |
| WO | WO-01/32197 A3 | 5/2001 |
| WO | WO-01/35932 A2 | 5/2001 |
| WO | WO-01/35932 A3 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/60424 A3 | 8/2001 |
| WO | WO-01/66044 A2 | 9/2001 |
| WO | WO-01/66044 A3 | 9/2001 |
| WO | WO-01/66130 A1 | 9/2001 |
| WO | WO-01/68135 A2 | 9/2001 |
| WO | WO-01/68135 A3 | 9/2001 |
| WO | WO-02/00244 A2 | 1/2002 |
| WO | WO-02/00244 A3 | 1/2002 |
| WO | WO-02/00272 A2 | 1/2002 |
| WO | WO-02/00272 A3 | 1/2002 |
| WO | WO-02/36147 A1 | 5/2002 |
| WO | WO-02/062405 A2 | 8/2002 |
| WO | WO-02/062405 A3 | 8/2002 |
| WO | WO-02/067978 A1 | 9/2002 |
| WO | WO-02/070029 A2 | 9/2002 |
| WO | WO-02/070029 A3 | 9/2002 |
| WO | WO-02/102783 A1 | 12/2002 |
| WO | WO-03/006025 A1 | 1/2003 |
| WO | WO-03/043576 A2 | 5/2003 |
| WO | WO-03/043576 A3 | 5/2003 |
| WO | WO-03/065996 A2 | 8/2003 |
| WO | WO-03/065996 A3 | 8/2003 |
| WO | WO-03/070186 A2 | 8/2003 |
| WO | WO-03/070186 A3 | 8/2003 |
| WO | WO-03/071997 A1 | 9/2003 |
| WO | WO-2004/002539 A2 | 1/2004 |
| WO | WO-2004/002539 A3 | 1/2004 |
| WO | WO-2004/002539 C1 | 1/2004 |
| WO | WO-2004/010907 A1 | 2/2004 |
| WO | WO-2004/071543 A1 | 8/2004 |
| WO | WO-2004/073563 A2 | 9/2004 |
| WO | WO-2004/073563 A3 | 9/2004 |
| WO | WO-2004/110308 A2 | 12/2004 |
| WO | WO-2004/110308 A3 | 12/2004 |

(56) References Cited

FOREIGN PATENT DOCUMENTS

| WO | WO-2004/110308 C2 | 2/2005 |
|---|---|---|
| WO | WO-2005/009496 A1 | 2/2005 |
| WO | WO-2005/032461 A2 | 4/2005 |
| WO | WO-2005/032461 A3 | 4/2005 |
| WO | WO-2005/042048 A2 | 5/2005 |
| WO | WO-2005/042048 A3 | 5/2005 |
| WO | WO-2005/046746 A2 | 5/2005 |
| WO | WO-2005/054279 A1 | 6/2005 |
| WO | WO-2005/054279 C1 | 6/2005 |
| WO | WO-2005/072656 A1 | 8/2005 |
| WO | WO-2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO-2006/044334 A2 | 4/2006 |
| WO | WO-2006/044334 A3 | 4/2006 |
| WO | WO-2006/050493 A2 | 5/2006 |
| WO | WO-2006/050493 A3 | 5/2006 |
| WO | WO-2006/093808 A1 | 9/2006 |
| WO | WO-2006/133403 A2 | 12/2006 |
| WO | WO-2006/133403 A3 | 12/2006 |
| WO | WO-2007/061889 A2 | 5/2007 |
| WO | WO-2007/061889 A3 | 5/2007 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO-2007/092622 A2 | 8/2007 |
| WO | WO-2007/092622 A3 | 8/2007 |
| WO | WO-2008/005427 A2 | 1/2008 |
| WO | WO-2008/005427 A3 | 1/2008 |
| WO | WO-2008/073628 A2 | 6/2008 |
| WO | WO-2008/073628 A3 | 6/2008 |
| WO | WO-2008/103690 A2 | 8/2008 |
| WO | WO-2008/103690 A3 | 8/2008 |
| WO | WO-2008/151193 A1 | 12/2008 |
| WO | WO-2009/100454 A1 | 8/2009 |
| WO | WO-2010/030714 A2 | 3/2010 |
| WO | WO-2010/071857 A1 | 6/2010 |
| WO | WO-2010/102266 A1 | 9/2010 |

OTHER PUBLICATIONS

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7):971-977.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

American Dental Association (Jun. 2006). Expert Panel Recommendations: Dental Management of Patients on Oral Bisphosphonate Therapy, *Report of the Council of Scientific Affairs*, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res.* 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-756.

Anusaksathien et al. "Effect of Sustained Gene Delivery of Platelet-Derived Growth Factor or Its Antagonist (PDGF—1308) on Tissue-Engineered Cementum," *J. Periodontal*, Mar. 2004, 75(3):429-440.

Arm, D.M. et al. "Effect of Controlled Release of Platelet-derived Growth Factor from a Porous Hydroxyapatite Implant on Bone Ingrowth," *Biomaterials*, 1996, 17(7):703-709.

Assael, L.A. (2006). "A Time for Perspective on Bisphosphonates," *J. Oral Maxillofac. Surg.* 64:877-879.

Babbush, C.A. DDS MSCD et al. "An in Vitro and in Vivo Evaluation of Autologous Platelet Concentrate in Oral Reconstruction," *Implant Dent.*, 2003, 12(1):24-34.

Barker, K. et al. (Jun. 2006). "Bisphosphonate-Associated Osteonecrosis of the Jaws: A Guide for the General Dental Practitioner," *Dental Update* pp. 270-275.

Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.

Bateman, J. et al. "Platelet-Derived Growth Factor Enhancement of Two Alloplastic Bone Matrices," *J. Periodontol.* (Nov. 2005) 76(11):1833-1841.

Becker. W. et al. (Nov. 1992). "A Comparison of ePTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol.* 63(11):929-940.

Berlemann, U. et al. (2002). "Adjacent Vertebral Failure After Vertebroplasty," *J. Bone Joint Surg. BR* 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedtl.htm&StoryID=76&>, last visited on May 18, 2010, 5 pages.

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.

Biomimetic Therapeutics (Jul. 15, 2004). "BioMimetic Pharmaceuticals' Receives Approvable Recommendation from FDA Advisory Panel for GEM 21S®," located at <http://biomimetics.com/cgi-bin/aw/acuweb.cgi?s=biomimetics&t=pressreleasedtl.htm&StoryID=78&>, last visited on May 18, 2010, 6 pages.

Biomimetic Therapeutics (Nov. 4, 2004). "BioMimetic Pharmaceuticals Raises $25.7 Million in Series C Financing," located at

(56) References Cited

OTHER PUBLICATIONS

<http://biomimetics.com/cgi-bin/aw/acuweb.cgi?s=biomimetics&t=pressreleasedtl.htm&StoryID=79&>, last visited on May 20, 2010, 5 pages.
Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.
Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasedtl.htm&StoryID=81&>, last visited on May 20, 2010, 6 pages.
Biomimetic Therapeutics (Nov. 21, 2005). "BioMimetic Therapeutics Announces FDA Approval of GEM 21S® Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.
Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.
Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166&>, 5 pages.
Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.
Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics&t=pressreleasedtl.htm&StoryID=94&>, last visited on May 18, 2010, 6 pages.
Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressreleasedtl.htm&StoryID=97&>, last visited on May 20, 2010, 6 pages.
Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID= 101 &>, last visited on May 18, 2010, 7 pages.
Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm&StoryID=104&>, last visited on May 18, 2010, 7 pages.
Biomimetic Therapeutics (Jan. 25, 2007). "BioMimetic Therapeutics Reports Positive Clinical Results Using GEM OS® 1 to Treat Distal Radius Fractures," located at <http://biomimetics.com/cgi-bin/aw/acuweb.cgi?s=biomimetics&t=pressreleasedtl.htm&StoryID=105&>, last visited on May 18, 2010, 6 pages.
Biomimetic Therapeutics (Feb. 21, 2007). "BioMimetic Therapeutics Receives Orphan Drug Designation for rhPDGF-BB Treatment of Osteonecrosis of the Jaw," located at < http://biomimetics.com/cgi-bin/aw/acuweb.cgi?s=biomimetics&t=pressreleasedtl.htm&StoryID=112&>, last visited on Apr. 5, 2010, 6 pages.

Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.
Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.
Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm&StoryID=116&>, last visited on May 18, 2010, 7 pages.
Biomimetic Therapeutics (Jun. 7, 2007). "BioMimetic Therapeutics Initiates Enrollment in E.U. Registration Trial for GEM OS®1 Bone Graft; U.S. GEM OS® 1 Pivotal Study Protocol Amended to Allow Shorter Follow-Up Time and More Patients," located at <http://biomimetics.com/cgi-bin/aw/acuweb.cgi?s=biomimetics&t=pressreleasedtl.htm&StoryID=119&>, last visited on May 18, 2010, 6 pages.
Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics&t=pressreleasedtl.htm&StoryID=123&>, last visited on May 18, 2010, 8 pages.
Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressreleasedtl.htm&StoryID=125&>, last visited on May 18, 2010, 7 pages.
Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressreleasedtl.htm&StoryID=127&>, last visited on May 18, 2010, 7 pages.
Biomimetic Therapeutics (Dec. 13, 2007). "BioMimetic Therapeutics reports Positive Clinical Results for GEM OS® 1 in Canadian Foot and Ankle Fusion Study; Clinical Success Rate of 90% Achieved in High Risk Patient Population," located at <http://biomimetics.com/cgi-bin/aw/acuweb.cgi?s=biomimetics&t=pressreleasedtl.htm&StoryID= 131 &>, last visited on May 18, 2010, 6 pages.
Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm&StoryID=149&>, last visited on May 18, 2010, 7 pages.
Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136&>, last visited on May 18, 2010, 6 pages.
Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.
Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.
Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/

(56) References Cited

OTHER PUBLICATIONS acuweb.cgi?s=biomimetics&t=pressreleasedtl.htm&StoryID=151&>, last visited on May 18, 2010, 8 pages.
Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&StoryID=153&>, last visited on May 18, 2010, 7 pages.
Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.
Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressreleasedtl.htm&StoryID=157&>, last visited on May 18, 2010, 8 pages.
Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.
Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.
Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.
Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.
Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.
Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.
Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.
Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at < http://biomimetics.com/cgi-bin/aw/acuweb.cgi?s=biomimetics&t=pressreleasedtl.htm&StoryID=188&>, last visited on May 18, 2010, 8 pages.
Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressreleasedtl.htm&StoryID=190&>, last visited on May 18, 2010, 6 pages.
Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm&StoryID= 191 &>, last visited on May 18, 2010, 8 pages.
Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 18, 2010, 5 pages.
Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.
Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.
Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.
Biomimetic Therapeutics (Mar. 12, 2010). "Morningstar® Document ResearchSM Form 10-K," United States Securities and Exchange Commission Annual Report, located at <http://investor.biomimetics.com/phoenix.zhtml?c=196896&p=irol-sec>, last visited on May 19, 2010, 247 pages.
Björkenheim, J-M. (1989). "Structure and Function of the Rabbit's Supraspinatus Muscle After Resection of its Tendon," *Acta Orthop. Scand.* 60(4):461-463.
Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.
Bolander, "Regulation of Fracture Repair by Growth Factors," *P.S.E.B.M.*, 1992, 200:165-170.
Bonfini, T. et al. (Jan. 1, 2006). "Autologous Marrow and Platel Gel in Bone Tissue Regeneration," *Cytotherapy* 8(1), Abstract No. 239, 2 pages.
Bora, F.W. Jr. et al. (Aug. 1987). "Joint Physiology, Cartilage Metabolism, and the Etiology of Osteoarthritis," *Hand Clin.* 3(3):325-336.
Boyden, E.M. et al. (Aug. 1995). "Late Versus Early Repair of Achilles Tendon Rupture: Clinical and Biomechanical Evaluation," *Clin. Orthop. Relat. Res.* 317:150-158.
Braddock, M. et al. (Oct. 2001). "Born Again Bone: Tissue Engineering for Bone Repair," *News Physiool. Sci.* 16:208-213.
Buser, D. et al. (1991). "Effects of Growth Factors on Bone Regeneration Around Titanium Implants," Abstract No. 282, *J. Dental Res.* 70:301.
Business Wire (Dec. 15, 2000). "Orthovita Recieves U.S. FDA Clearance for Vitoss Scaffold, the First Engineered 90% Porous Beta-Tricalcium Phosphate; Another Milestone Achievement This Year for Orthovita," located at <http://www.highbeam.com/doc/1G1-68027113.html>, last visited on Apr. 26, 2010, 3 pages.
Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3 pages.
Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

(56) References Cited

OTHER PUBLICATIONS

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry*. 2001, 21(2):109-120.

Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol*. 71(1):1743-1749.

Catalano, L. et al. (2006). "Bisphoshonates and Risk of Osteonecorisis of the Jaws," *Haema* 9(3):410-414.

Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand*. 74(5):559-564.

Cenni, E. et al. (2005, e-pub. Feb. 1, 2005). "Plasma Levels of Platelet-Derived Growth Factor BB and Transforming Growth Factor in Patients with Failed Hip Prostheses," *Acta Orthopaedica* 76(1):64-66.

Chalmers, J. (Jun. 2000). "Review Article: Treatment of Achilles Tendon Ruptures," *J. Orthop. Surg*. 8(1):97-99.

Chan, B.P. et al. (Jul. 2006). "Supplementation-time Dependence of Growth Factors in Promoting Tendon Healing," *Clinical Orthopaedics and Related Research* 448:240-247.

Chen et al. "Adenoviral Gene Transfer of PDGF Downregulates Gas Gene Product PDGFR and Prolongs ERK and AktIPKB Activation," *Am J Physiol Cell Physiol.*, Mar. 2002, 282:C538-C544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.

Cho et al. (Jun. 1995). "Platelet Derived Growth Factor—Modulated Guided Tissue Regenerative Therapy," *J. Peridontol.* 66(6):522-530.

Clain, M.R. et al. (Oct. 1992). "Achilles Tendinitis," *Foot Ankle Int.* 13(8):482-487.

Clergeau, L.P. et al. (Feb. 1996). "Healing Response to Anorganic Bone Implantation in Periodontal Intrabony Defects in Dogs Part 1. Bone Regeneration. A Microradiographic Study," *J. Periodontool.* 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res.* 82:253-262.

Cooke et al. "Effect of rhPDGR-BB Delivery on Mediators of Periodontal Wound Repair," *Tissue Engineering*, 2006, 12(6):1441-1450.

Cossolin, G.S.I. et al. ( Date Unknown) "Treatment of Avascular Osteonecrosis of the Jaws in Cancer Patients with a Histroy of Bisphosphonate Therapy by Combining Bone Resection and Autologous Platelet-Rich Plasma," *Hospital Santa Catarina* 10 pages.

Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.

Courneya, J-P. et al. (2010). "Normal and Diseased Primary Human Tenocytes in Response to rhPDGF-BB," Poster No. 1118, 56th Annual Meeting of the Orhopaedic Research Society, located at < http://www.ors.org/web/Transactions/56/1118.pdf>, last visited on Feb. 23, 2010, 1 page.

Creaney, L. et al. (May 2008, e-pub. Nov. 5, 2007). "Growth Factor Delivery Methods in the Management of Sports Injuries: The State of Play," *Br. J. Sports Med.* 42(5):314-320, Abstract Only.

Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (c-sis) of the Simian Sarcoma Virus onc Gene," *Science* 218:686-688.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Dines J.S. et al. (Sep./Oct. 2007). "Tissue Engineering and Rotator Cuff Tendon Healing," *J. Shoulder Elbow Surg.* 16(5S):204S-207S.

Dines, J.S. et al. (Sep./Oct. 2007). "The Effect of Growth on Differentiation Factor-5-Coated Sutures on Tendon Repair in a Rat Model," *J. Shoulder Elbow Surg.* 16(5S):215S-221S.

Donnelly, B.P. et al. (Jul. 2006). "Nucleotide Structure of Equine Platelet-Derived Growth Factor-A and -B and Expression in Horses with Induced Acute Tendinitis," *Am. J. Vet. Res.* 67(7):1218-1225, Abstract Only.

Doolittle et al. (Jul. 15, 1983). "Simian Sarcoma Virus one Gene v-sis, Is Derived from the Gene (or Genes) Encoding a Platelet-Derived Growth Factor," *Science* 221:275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res.* 6(3):207-215.

Erikson, A. et al. (Nov. 5, 1991). "Induction of Platelet-Derived Growth Factor α- and β-Receptor mRNA and Protein by Platelet Derived Growth Factor BB," *J. Biol. Chem.* 266(31):21138-21144.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," The BBI Newsletter, located at <http://findarticles.com/p/articles/mi_m3570/is_n9_v21/ai_n27541529>, last visited on Mar. 12, 2009, 2 pages.

(56) References Cited

OTHER PUBLICATIONS

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol.* 32:1123-1128.

Finkelman, R.D. et al. (1995). "Systematic PDGF ± Alendronate Increases Bone Density in OVX Rats," Abstract No. 1281, *J. Dental Res.* 74:172.

Fontana et al. "Effect of Platelet-Rich Plasma on the Pert-implant Bone Response: An Experimental Study," *Implant Dentistry*, 2004, 13:73-78.

Franco, B. et al. (Jan.-Jun. 2008). "Tissue Engineering Approaches for the Construction of a Completely Autologous Tendon Substitute," *Indian J. Plast. Surg.* 41(1):38-46, 13 pages.

Freedonia (Sep. 2006). "Biocompatible Materials. US Industry Study with Forecasts to 2010 & 2015," Study #2111, located at < http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," *Spine* 29(20):2270-2276.

Fukui, A. et al. (Sep. 1993). "Isolation and Characterization of *Xenopus* activin and Follistatin," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86A(2):219-244.

Gamradt, S.C. et al. (Mar. 2007). "Platelet Rich Plasma in Rotator Cuff Repair," *Tech. In Orthop.* 22(1):26-33.

Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An in Vivo Biomechanic Study at 3 Weeks in Canines," *J. Hand Surg. Am.* 32A(3):373-379.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors -I (IGF-I) with Other Growth Factors on Bone Formation in vitro," Abstract No. 831, *J. Dental Res.* 73:205.

Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.

Giannobile, W.V. et al. (Nov. 1995). "Platelet Derived Growth Factor (PDGF) and Insulin-Like Growth Factor (IGF-I) Enhances Periodontal Regeneration in Macaca fascicularis," Abstract No. 28, *Advanced Dental Research* 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," Bone, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Periodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Giddings, V.L. et al. (2000). "Calcaneal Loading During Walking and Running," *Med. Sci. Sports Exerc.* 32(3):627-634.

Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.

Goutallier, D. et al. (Jul. 1994). "Fatty Muscle Degeneration in Cuff Ruptures: Pre- and Postoperative Evaluation by CT Scan," *Clin. Orthop.* 304:78-83.

Grageda, "Platelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-α and β-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs of the Rotator Cuff," *J. Bone Joint Surg. Am.* 73-A(7):982-989.

Hart et al. "Synthesis, Phosphorylation, and Degradation of Multiple Forms of the Platelet-derived Growth Factor Receptor Studied Using a Monoclonal Antibody," *The Journal of Biological Chemistry*, Aug. 5, 1987, 262(22):10780-10785.

Hart et al. "Two Classes of PDGF Receptor Recognize Different Isoforms of PDGF," *Science*, Jun. 1988, 240:1529-1531.

Hart, C.E. et al. "Purification of PDGF-AB and PDGF-BB from Human Platelet Extracts and Identification of All Three PDGF Dimers in Human Platelets," *Biochemistry*, Jan. 9, 1990, 29(1):166-172.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub. Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Hess, G.W. (Feb. 2010). "Achilles Tendon Rupture: a Review of the Etiology, Population, Anatomy, Risk Factors, and Injury Prevention," *Foot Ankle Spec.* 3(1):29-32.

Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.

Hildebrand, K.A. et al. (1998). "The Effects of Platelet-Derived Growth Factor-BB on Healing of the Rabbit Medial Collateral Ligament. An in Vivo Study," *American Journal of Sports Medicine* 26(4):549-554.

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

(56) References Cited

OTHER PUBLICATIONS

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.
Hollinger, J.O. et al. (Feb. 2008). "Recombinant Human Platelet Derived Growth Factor: Biology and Clinical Applications," *J. Bone & Joint Surgery* 90-A(Suppl. 1):48-54.
Hollinger, J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.
Hollinger, J.O. et al. (2008). "Protein Therapeutics and Bone Healing," Chapter 1 in *Tissue Engineering: Applications in Maxillofacial Surgery and Periodontics*, Second Edition, Lynch,.S.E. et al. eds., Quintessence Publishing Co.: Hanover Park, IL, pp. 3-25.
Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.
Howell, T.H. et al. (1996). "Polypeptide Growth Factors for Periodontal Regeneration," *Current Opinion in Periodontology* 3:149-156.
Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.
Howes et al. "Platelet-Derived Growth Factor Enhances Demineralized Bone Matrix-Induced Cartilage and Bone Formation," *Calcif Tissue Int.*, 1988, 42:34-38.
Huang, L.-H. et al. "The Effect of Platelet-Rich Plasma on the Coronally Advanced Flap Root Coverage Procedure: A Pilot Human Trial," *J. Periodontal*, Oct. 2005, 76(10):1768-1777.
Hsu et al. (Jul. 2004). "Clinical Implications of Growth Factors in Flexor Tendon Wound Healing," *The Journal of Hand Surgery* 29A(4):551-563.
Ignotz, R.A. et al. (Mar. 25, 1986). "Transforming Growth Factor-βSimulates the Expression of Fibronectin and Collagen and Their Incorporation in the Extracellular Matrix," *J. Bio.Chem.*261(9):4337-4345.
Ikezawa et al. "Characterization of Cementum Derived Growth Factor as an Insulin-Like Growth Factor-I Like Molecule," *Connective Tissue Research*, 1997, 36(4):309-319.
Inglis, A.E. et al. (Oct. 1976). "Ruptures of the Tendo Achilles: An Objective Assessment of Surgical and Non-Surgical Treatment," *J. Bone Joint Surg.* 58A(7):990-993.
Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.
Jensen et al. "Platelet rich plasma and fresh frozen bone allograft as enhancement of implant fixation—an experimental study in dogs," *Journal of Orthopaedic Research*, 2004, 22:653-658.
Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.
Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.
Jiang, D. et al. "Modification of an Osteoconductive Anorganic Bovine Bone Miami Matrix with Growth Factors," *J. Periodonlol.*, Aug. 1999, 70(8):834-839.
Jin et al. "Engineering of Tooth-Supporting Structures by Delivery of PDGF Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis in Vivo," *PLoS ONE* 3(3):e1729, pp. 1-9.
Jones et al. (1992). "Isolation of Vgr-2, a Novel Member of the Transforming Growth Factor-Beta-related Gene Family," *Mol Endocnnol.* 6(11):1961-1968.
Jozsa, L. et al. (Aug. 1989). "Fibronectin and Laminin in Achilles Tendon," *Acta Orthop Sacninavica* 60(4):469-471.
Kademani, D. et al. (Aug. 2006). "Primary Surgical Therapy for Osteonecrosis of the Jaw Secondary to Bisphosphonate Therapy," *Mayo Clin. Proc.* 81(8):1100-1103.
Kaigler, "Growth factor delivery for oral and periodontal tissue engineering," *Expert Opin Drug Deliv.*, 2006, 3(5):647-662.
Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.
Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.
Kazlauskas et al. "Different effects of homo- and heterodimers of platelet-derived growth factor a and B chains on human and mouse fibroblasts," *The EMBO Journal* (1988) 7(12):3727-3735.
Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.
Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.
Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.
Kobayashi, M. et al. (May/Jun. 2006). "Expression of Growth Factors in Early Phase of Supraspinatus Tendon Healing in Rabbits," *J. Shoulder Elbow Surg.* 15(3):371-377.
Kovacevic, D. et al. (Mar. 2008). "Biological Augmentation of Rotator Cuff Tendon Repair," *Clin. Orthop. Relat. Res.* 466(3):622-633.
Kovacs et al. "Comparative Study of β-Tricalclum Phosphate Mixed with Platelet-Rich Plasma versus β-Tricalcium Phosphate, a Bone Substitute Material in Dentistry," *Acts Veterinaria Hungarica*, 2003, 51(4):475-484.
Landesberg et al. "Quantification of Growth Factor Levels Using a Simplified Method of Platelet-Rich Plasma Gel Preparation," *J. Oral Maxillofac. Surg.*, 2000, 58:297-301.
Lasa et al. "Delivery of Demineralized Bone Powder by Fibrin Sealant," *Plast. Reconstr. Surg.*, 1995, 96(6):1409-1417.
Lasa Jr., C. et al. (1996). "Bone Induction by Demineralized Bone Powder and Partially Purified Osteogenin Using a Fibrin-Sealant Carrier," Chapter 14 in *Surgical Adhesives and Sealants: Current Technology and Applications*, Sierra, D. et al. eds., Technomic Publishing.Company, Inc.: Lancaster, PA, pp. 135-144.
Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.
Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.
Lee et al. "Enhanced bone formation by controlled growth factor delivery from chitosan-based biomaterials," *Journal of Controlled Release*, 2002, 78: 187-197.
Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

(56) References Cited

OTHER PUBLICATIONS

Letson, A.K. et al. (1994). "The Effect of Combinations of Growth Factors on Ligament Healing," *Clinical Orhopaedics and Related Research* 308:207-212.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO. , Sep. 9-13, 1994, p. S135.

Liang et al. (Sep. 2000). "Effect of Cytokines on Repair of Tendon Injury," *Pub Med* 14(5):283-285, Abstract Only.

Liang, H.W. et al. (Aug. 2009). "Effect of Platelet-Derived Growth Factor-BB on Proliferation of Tendon Cells Cultured in vitro," *Zhonghua Shao Shang Za Zhi* 25(4):298-300, Abstract Only.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation by GBR: an experimental study in rats," *J. Clin. Periodontol.*, 2005, 32:1247-1253.

Lioubavina-Hack et al. "Effect of Bio-Oss® with or without platelet-derived growth factor on bone formation by 'guided tissue regeneration': a pilot study in rats," *J Clin. Periodontol*, 2005, 32(12):1254-1260.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," *Executive Committee on Chemotherpeutics; Amer. Acad Peridontal—Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. (1991). "Platelet-Derived Growth Factor and Insulin-Like Growth Factor. I: Mediators of Healing Soft Tissue and Bone Wounds," *Periodontol Case Reports NE Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration* Abstract, 2(1):84.

Lynch, S.E. et al. (1994). "Polypeptide Growth Factors: Molecular Mediators of Tissue Repair," Chapter 33 in *Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 in *Periodontal Regeneration: Current Status and Directions*, Polson, A. ed. Quintessence Publishing Co, Inc: Chicago, IL, 11:179-197.

Lynch, S.E. (1995). "Introduction," in *Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 in *Bone Regeneration and Repair: Biology and Clinical Applications*, Lieberman, J.R. et al. eds., Humana Press Inc.: Totowa, NJ, pp. 359-390.

Lynch, S.E. et al. (Dec. 2006). "A New Era in Periodontal and Periimplant Regeneration: Use of Growth-Factor Enhanced Matrices Incorporating rhPDGF," *Compendium of Continuing Education in Dentistry* 27(12):672-679.

Lynch, S.E. et al. (2008). "Use of rhPDGF to Improve Bone and Periodontal Regeneration," Chapter 6 in *Tissue Engineering: Applications in Maxillofacial Surgery and Periodontics*, Second Edition, Lynch, S.E. et al. eds., Quintessence Publishing Co.: Hanover Park, IL, pp. 87-102.

Maffulli, N. et al. (2002). "Tendon Healing: Can It Be Optimized?" *British Journal of Sports Medicine* 36:315-316.

Maffulli, N. et al. (2003). "Types and Epidemiology of Tendinopathy," *Clinics in Sports Medicine* 22:675-692.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 in *Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 in *Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with Anorganic Bovine Bone in the Chimpanzee," *The International Journal of Oral & Maxillofacial Implants*, 1999, 14(3):361-368.

McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

(56) References Cited

OTHER PUBLICATIONS

McGuire, M.K. (2008). "Soft Tissue Engineering Applications in Dentistry," Chapter 7 in *Tissue Engineering: Applications in Maxillofacial Surgery and Periodontics*, Second Edition, Lynch, S.E. et al. eds., Quintessence Publishing Co.: Hanover Park, IL, pp. 103-118.

McMurty, R.Y. et al. (1992). "Fractures of the Distal Radius," Chapter 35 in *Skeletal Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:1675-1681.

Migliorati, C.A. et al. (Jun. 2006). "Bisphosphate-Associated Osteonecrosis: A Long Term Complication of Bisphophonate Treatment," *Lancet Oncol.* 7:508-514.

Millette, E. et al. (2006). "Platelet-Derived Growth Factor-BB Transactivates the Fibroblast Growth Factor Receptor to Induce Proliferation in Human Smooth Muscle Cells," *Trends Cardiov. Med.* 16(1):25-28.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in in Vitro Wound Model," *J. Periodontal.* 72(3):331-340.

Nakamura, N. et al. (1998). "Early Biological Effect of in Vivo Gene Transfer of Platelet-derived Grown Factor (PDGF)-B into Healing Patellar Ligament," *Gene Therapy* 5:1165-1170.

Nancollas, G.H. et al. (2006, e-pub. Jul. 20, 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins et al. "Periodontal Regeneration in Humans Using Recombinant Human Platelet-derived Growth Factor-BB (rhPDGF-BB) and Allogenic Bone," *J. Periodontal*, Sep. 2003, 74(9):1282-1292.

Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4):365-373.

Nevins et al. "Platelet-Derived Growth Factor Stimulates Bone Fill and Rate of Attachment Level Gain: Results of a Large Multicenter Randomized Controlled Trial," *J. Periodontal*, Dec. 2005, 76(12):2205-2215.

Nevins, M. et al. (Oct. 2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nevins, M. et al. (2008). "Treatment of Advanced Periodontal Defects Using Bioactive Therapies," Chapter 5 in *Tissue Engineering: Applications in Maxillofacial Surgery and Periodontics*, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 in *Tissue Engineering: Applications in Maxillofacial Surgery and Periodontics*, Second Edition, Lynch, S.E. et al. eds., Quintessence Publishing Co.: Hanover Park, IL, pp. 119-131.

Nickols, J.C. et al. (2008). "The Role of Growth Factors in Tendon Healing," Chapter 20 in *Tissue Engineering: Applications in Maxillofacial Surgery and Periodontics*, Second Edition, Lynch, S.E. et al. eds., Quintessence Publishing Co.: Hanover Park, IL, pp. 276-289.

Nistor, L. (Mar. 1981). "Surgical and Non-Surgical Treatment of Achilles Tendon Rupture: A Prospective Randomized Study," *J. Bone Joint Surg Am.* 63A(3):394-399.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," *International Journal of Oral and Maxillofacial Surgery* 23(2):110-114, abstract only.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary. Vitoss™ Scaffold Syntehtic Cancellous Bone Void Filler," located at <http://www.accessdata.fda.gov/cdrh_docs/pdf/k994337.pdf>, last visited on Mar. 30, 2010, 6 pages.

Orthovita, Inc. (Nov. 19, 2002). "Morningstar® Document Research™. Form 10-Q, Quarterly Repot Which Provides a Continuing View of a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedures—Guided Tissue Regeneration and Demineralized Freeze-Dried Bone Allograft—in the Treatment of Intrabony Defects: A Clinical and Radiographic Study," *J. Periodontol.* 69(7):751-758.

Park et al. (Jun. 1995). "Periodontal Regeneration in Class III Furcation Defects of Beagle Dogs Using Guided Tissue Regenerative Therapy with Platelet-Derived Growth Factor," *J. Periodontol.* 66:462-477.

Paul, W. et al. (1999). "Development of Porous Spherical Hydroxyapatite Granules: Application Towards Protein Delivery," *J. Mater. Sci. Mater. Med.* 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol.* 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts," *Arch. Orthop. Trauma Surg.* 123(9):485-488.

Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor β," *Endocrinology* 127(1):69-75.

(56) References Cited

OTHER PUBLICATIONS

Philippart et al. "Human Recombinant Tissue Factor, Platelet-rich Plasma, and Tetracycline Induce a High-Quality Human Bone Graft a 5-year Survey," *The International Journal of Oral and Maxillofacial Implants*, 2003, 18(3):411-416.

Phillips, S. et al. (1988). "The Direct Medical Costs of Osteoporosis for American Woman Aged 45 and Older, 1986," *Bone* 9(4):271-279.

Pickett, F.A. (Jul. 2006). "Bisphosphonate-Associated Osteonecrosis of the Jaw: A Literature Review and Clinical Practice Guidelines," *Journal of Dental Hygiene* 80(3):1-12.

Pietrzak, W.S. et al. (Jul. 2000). "Calcium Sulfate Bone Void Filler: A Review and a Look Ahead," *J. Craniofac. Surg.* 11(4):327-333; discussion p. 334.

Polverini, P.J. (Aug. 2002). "Angiogenesis in Health and Disease: Insights into Basic Mechanisms and Therapeutic Opportunities," *Journal of Dental Education* 66(8):962-975.

Premdas, J. et al. (2001). "The Presence of Smooth Muscle Action in Fibroblasts in the Torn Human Rotator Cuff," *Journal of Orthopaedic Research* 19:221-228.

Qiu, Y. et al. (2009). "Combination of PDGF-BB and bFGF Reduces Differentiation but Maintains Proliferation of Human Tenocytes in Low Bovine Serum Culture in vitro," *European Cells and Materials* 18(Suppl. 2):86.

Qu, Z. et al. (Nov. 1994). "Immunolocalization of Basic Fibroblast Growth Factor and Platelet-Derived Growth Factor-A During Adjuvant Arthritis in the Lewis Rat," *Am. J. Pathol.* 145(5):1127-1139.

R&D Systems, Inc. (Date Unknown). "Quantikine® Human PDGF-BB Immunoassay," *Package Insert*, Catalog No. DBB00, SBB, and PDB00, located at <http://www.rndsystems.com/pdf/dbb00.pdf>, last visited on Mar. 30, 2010, 16 pages.

Rao, C.D. et al. (Apr. 1986). "Structure and Sequence of the Human c-sis/Platelet-Derived Growth Factor 2 (SIS/PDGF2) Transcriptional Unit," *Proc. Natl. Acad. Sci. USA* 83:2392-2396.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med.* 23(3):407-413, Abstract Only, 2 pages.

Rasubala, L. et al. "Platelet-derived Growth Factor and Bone Morphogenetic Protein in the Healing of Mandibular Fractures in Rats," *British Journal of Oral and Maxillofacial Surgery*, 2003, 41:173-178.

Rettig, A.C. et al. (2005). "Potential Risk of Rerupture in Primary Achilles Tendon Repair in Athletes Younger Than 30 Years of Age," *Am. J. Sports Med.* 33(1):119-123.

Rickert, M. et al. (2001). "A Growth and Differentiation Factor-5 (GDF-5)-Coated Suture Stimulates Tendon Healing in an Achilles Tendon Model in Rats," *Growth Factors* 19:115-126.

Riley, G. (2004, e-pub. Jul. 16, 2003). "The Pathogenesis of Tendinopathy. A Molecular Perspective," *Rheumatology* 43(2):131-142.

Robbins, K.C. et al. (Oct. 13, 1983). "Structural and Immunological Similarities Between Simian Sarcoma Virus Gene Product(s) and Human Platelet-Derived Growth Factor," *Nature* 305:605-608.

Rodeo, S.A. et al. (Dec. 1993). "Tendon Healing in a Bone Tunnel," *J. Bone Joint Surg. Am.* 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med.* 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61:157-163.

Rohrich et al. (Nov. 1999). "Mersilene Suture as a Vehicle for Delivery of Growth Factors in Tendon Repair," *Journal of the American Society of Plastic Surgeons* 104(6):1713-1717.

Rolf, C.G. et al. (2001). "Increased Cell Proliferation and Associated Expression of PDGFRβ Causing Hypercellularity in Patellar Tendinosis," *Rheumatology* 40:256-261.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.

Ruiz, G. et al. (1991). "Short Term Administration of Growth Factors Enhances Periodontal Regeneration," Abstract No. 1615, *J. Dental Res.* 70:468.

Russell, T.A. et al. (Date Unknown). "Trigen® IM Nail System Surgical Technique. Trochanteric Antegrade Nail (TAN™)," 24 pages.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.

Sakiyama-Elbert, S.E. et al. (Nov. 2008). "Controlled-Release Kinetics and Biologic Activity of Platelet-Derived Growth Factor-BB for Use in Flexor Tendon Repair," *J. Hand Surg. Am.* 33(9):1548-1557, Abstract Only.

Sandberg, "Matrix in Cartilage and Bone Development: Current Views on the Function and Regulation of Major Organic Components," *Annals of Medicine*, 1991, 23:207-217.

Sarment, D.P. et al. (Feb. 1, 2006). "Effect of rhPDGF-BB on Bone Turnover During Periodontal Repair," *Journal of Clinical Periodontolgy* 33(2):135-140.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.

Sasai, Y. et al. (Dec. 2, 1994). "Xenopus chordin: A Novel Dorsalizing Factor Activated by Organizer-Specific Homeobox Genes," *Cell* 79:779-790.

Saygin et al. "Molecular and Cell Biology of Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.

Schmidt et al. "A review of the effects of insulin-like growth factor and platelet derived growth factor on in vivo cartilage healing and repair," *Osteoarthritis and Cartilage*, 2006, 14(5):403-412.

Schmidt, M.B. et al. (2008). "Tissue Engineering Strategies in the Treatment of TMDs," Chapter 18 in *Tissue Engineering: Applications in Maxillofacial Surgery and Periodontics*, Second Edition, Lynch, S.E. et al. eds., Quintessence Publishing Co.: Hanover Park, IL, pp. 252-264.

Schmitt, J.M. et al. (Nov. 1997). "Comparison of Porous Bone Mineral and Biologically Active Glass in Critical-Sized Defects," *J. Periodontol.* 68(11):1043-1053.

Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.

secinfo.com (Mar. 31, 2003). "Interpore International Inc/DE 10-K for Dec. 31, 2002," located at <http://www.secinfo.com/dV179.2kp.htm, last visited on May 20, 2010, 57 pages.

Seeherman, H.J. et al. (Oct. 2008). "rhBMP-12 Accelerates Healing of Rotator Cuff Repairs in Sheep Model," *J. Bone Joint Surg. Am.* 90A(10):2206-2219.

Shahgaldi, B.F. et al. (Jan. 1991). "Repair of Cartilage Lesions Using Biological Implants. A Comparative Histological and Biomechanical Study in Goats," *J. Bone Joint Surg. Br.* 73-B(1):57-64.

Sharma, P. et al. (2008). "Tendinopathy and Tendon Injury: The Future," *Disability and Rehabilitation* 30(20-22):1733-1745.

Sigma (Date Unknown). "Platelet Derived Growth Factor-BB," Product Information Sheet, 2 pages.

Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.

(56) References Cited

OTHER PUBLICATIONS

Simion, M. et al. (1994). "Vertical Ridge Augmentation Using a Membrane Technique Associated with Osseointegrated Implants," *Int. J. Periodontics Restorative Dent.* 14(6):497-511.
Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.
Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.
Simion, M. et al. (1999). "Effect of Different Microstructures of e-PTFE Membranes on Bone Regeneration and Soft Tissue Response: A Histologic Study in Canine Mandible," *Clin. Oral Implants Res.* 10:73-84.
Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.
Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.
Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.
Smith & Nephew (Date Unknown). "Trigen. Humeral Nail," Surgical Technique Pamphlet, 27 pages.
Sode, J. et al. (May 2007, e-pub. Mar. 3, 2007). "Use of Fluroquinolone and Risk of Achilles Tendon Rupture: A Population-based Cohort Study," *Eur. J. Clin. Pharmacol.* 63(5):499-503.
Solheim, E. "Growth Factors in Bone," *International Orthopedics (SICOT)*, 1998, 22:410-416.
Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al. eds., Quintessence Publishing Co.: Hanover Park, IL, pp. 26-36.
Spindler, K.P. et al. (1995). "Proliferative Response to Platelet-Derived Growth Factor in Young and Old Rat Patellar Tendon," *Connective Tissue Research* 31(2):171-177.
Spindler, K.P. et al. (Jul. 1996). "Patellar Tendon and Anterior Cruciate Ligament Have Different Mitogenic Responses to Platelet-Derived Growth Factor and Transforming Growth Factor β," Journal of Orthopaedic Research 14(4):542-546.
Stephan, E.B. et al. (Apr. 1999). "Anogranic Bovine Bone Supports Osteoblastic Cell Attachment and Proliferation," *J. Periodontol.* 70(4):364-369.
Stephan et al. "Platelet-Derived Growth Factor Enhancement of a Mineral-Collagen Bone Substitute," *J. Periodontal*, Dec. 2000, 71:1887-1892.
Strom, T.B. (Sep. 6, 2005). "Saving Islets from Allograft Rejection," *PNAS USA* 102(36):12651-12652.
Suba et al. "Facilitation of β-Tricalcium Phosphate-Induced Alveolar Bone Regeneration by Platelet-Rich Plasma in Beagle Dogs: A Histologic and Histomorphometric Study," *The International J. of Oral and Maxillofacial Implants*, 2004, 19(6):832-838.
Tadic, D. et al. (2004). "A Novel Method to Produce Hydroxyapatite Objects with Interconnecting Porosity that Avoids Sintering," *Biomaterials* 25(16):3335-3340.
Tamai, N. et al. (2002). "Novel Hydroxyapatite Ceramics with an Interconnective Porous Structure Exhibit Superior Osteoconduction in vivo," *J. Biomed. Mater. Res.* 59:110-117.
Teraoka, K. et al. (2004). "Construction of an Interconnected Pore Network Using Hydroxyapatite Beads," *Key. Eng. Mater.* 254-256:257-259.
Teraoka, K. et al. (Sep. 2004). "Construction of Interconnected Pore Network Using Hydroxyapatite Small Components," *Trans. Mater. Res. Soc. Jpn.* 29(6):2919-2921.
Thompoulos, S. et al. (May 2005). "Effect of Several Growth Factors on Canine Flexor Tendon Fibroblast Proliferation and Collagen Synthesis in vitro," *J. Hand Surg. Am.* 30(3):441-447, Abstract Only.
Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.
Thomopoulos, S. et al. (Sep. 2009, e-pub. Mar. 25, 2009). "Enhanced Flexor Tendon Healing through Controlled Delivery of PDGF-BB," *J. Orthop. Res.* 27(9):1209-1215.
Thomopoulos, S. et al. (Feb. 2010, e-pub. Nov. 24, 2009). "bFGF and PDGF-BB for Tendon Repair: Controlled Release and Biologic Activity by Tendon Fibroblasts in Vitro," *Ann. Biomed. Eng.* 38(2):225-234.
Tinti, C. et al. (1996). "Vertical Ridge Augmentation: What is the Limit?" *Int. J. Periodontics Restorative Dent.* 16(3):221-229.
trending123.com (Date Unknown). "Stock Sectors. Medical Instruments Supls," located at <http://www.trending123.com/stock-sectors/Medical_Instruments_Supls.html>, last visited on May 3, 2010, 11 pages.
Uggen, J.C. et al. (Jan. 2005). "Tendon Gene Therapy Modulates the Local Repair Enviornment in the Shoulder," *J. Am. Osteopath. Assoc.* 105(1):20-21.
Uggen, C. et al. (2010). "The Effect of Recombinant Human Platelet-Derived Growth Factor BB-Coated Sutures on Rotator Cuff Healing in a Sheep Model," *Arthroscopy* 26(11):1456-1462.
U.S. Appl. No. 10/965,319, filed Oct. 14, 2004, by Lynch.
Van Den Wyngaert, T. et al. (Aug. 2006). "Bisphosphonates and Osteonecrosis of the Jaw: Cause and Effect or a post hoc Fallacy?" *Annals of Oncology* 17(8):1197-1204.
Venkatasatya, M. et al. (2008). The Effect of PDGF, Vitamin D and PTH on Osteoblasts Derived From Patients on Chronic Bisphosphonate Therapy , Dissertation for the State University of New York at Buffalo, located at <http://gradworks.umi.com/14/531/1453440.html>, last visited on Mar. 31, 2010, 2 pages, Abstract Only.
Virchenko, O. et al. (2008, e-pub. Jul. 4, 2008). "Early Achilles Tendon Healing in Sheep," *Arch. Orthop. Trauma Surg.* 128:1001-1006.
Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.
Walter, C. et al. (2006, e-pub. Aug. 29, 2006). "Prevalence of Bisphophonate Associated Osteonecrosis of the Jaw within the Filed of Osteonecrosis," *Support Care Center* 6 pages.
Wang, Y. et al. (Feb. 23, 1996). "A Large Family of Putative Transmembrane Receptors Homologous to the Product of the Drosophila Tissue Polarity Gene Frizzled," *J. Biol. Chem.* 271(8):4468-4476.
Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.
Wang, X.T. et al. (Sep. 2004). "Tendon Healing in Vitro: Genetic Modification of Tenocytes With Exogenous PDGF Gene and Promotion of Collagen Gene Expression," *The Journal of Hand Surgery* 29A(5):884-890.
Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.
Wei et al. "Nano-Fibrous Scaffold for Controlled Delivery of Recombinant Human PDGF-BB," *Journal of Controlled Release*, 2006, e-pub. Mar. 3, 2006, 112:103-110.
Weiler, A. et al. (2004). "The Influence of Locally Applied Platelet-Derived Growth Factor-BB on Free Tendon Graft Remodeling After Anterior Cruciate Ligament Reconstruction," *Am. J. Sports Med.* 32(4):881-891.

(56) References Cited

OTHER PUBLICATIONS

White, E. et al. (1986). "Biomaterial Aspects of Interpore-200 Porous Hydroxyapatite," *Dent. Clin. North Am.* 30(1):49-67, Abstract only.
Wiesen, R.J. et al. (1998). "Efficacy of Bovine Bone Mineral in Vertical Osseous Defects," Abstract No. 1165, *J. Dental Res.* 77:777.
Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.
Wikesjö et al. (1989). "Effects of Subgingival Irrigation on A. actinomycetemcomitans," *J. Clin. Perrodont.* 16:116-119.
Williams et al. "Tissue Engineering: What Does It Mean? Why Is It Important?" *Compendium*, Jan. 2005, 26(1):54-60.
Wisner-Lynch, L.A. (Oct. 2006). "From Passive to Active: Will Recombinant Growth Factor Therapeutics Revolutionize Regeneration?" *Int. J. Periodont. and Rest. Dent.* 26(5):409-411.
Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.
Woo, S.L-Y. et al. (1998). "Engineering the Healing of the Rabbit Medical Collateral Ligament," *Medical and Biological Engineering and Computing* 36:359-364.
Woo, S-B. et al. (May 16, 2006). "Systematic Review: Bisphosphonates and Osteonecrosis of the Jaws," *Annals of Internal Medicine* 144(10):753-761.
Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.
Yazawa et al. "Basic Studies on the Clinical Applications of Platelet-Rich Plasma," *Cell Transplantation*, 2003, 12:509-518.
Yazawa, M. et al. (May 2004). "Basic Studies on the Bone Formation Ability by Platelet Rich Plasma in Rabbits," *Journal of Craniofacial Surgery* 15(3):439-446.
Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.
Younger, E.M. et al. (1989). "Morbidity at Bone Graft Donor Sites," *J. Orthop. Trauma* 3(3):192-195.
Zavras, A.I. et al. (2006). "Bisphosphonates Are Associated With Increased Risk for Jaw Surgery in Medical Claims Data: Is it Osteonecrosis?" *J. Oral Maxillofac. Surg.* 64:917-923.
Zhu et al. "Gene Transfer and Expression of Platelet-Derived Growth Factors Modulate Periodontal Cellular Activity," *J. Dent Res*, 2001, 80(3):892-897.
Zimmer, Inc. (2005). "Zimmer® Collagen Repair Patch," Product No. 04-4100-001-00, 6 pages.
Advisory Action Before the Filing of an Appeal Brief dated Apr. 4, 2008, for U.S. Appl. No. 11/159,533, filed Jun. 23, 2005, 3 pages.
Advisory Action Before the Filing of an Appeal Brief dated Jun. 4, 2008, for U.S. Appl. No. 11/159,533, filed Jun. 23, 2005, 3 pages.
Amendment After Request for Continued Examination dated Aug. 7, 2008, for U.S. Appl. No. 11/159,533, filed Jun. 23, 2005, 18 pages.
Amendment and Response to Final Office Action dated Feb. 25, 2008, for U.S. Appl. No. 11/159,533, filed Jun. 23, 2005, 9 pages.
Amendment and Response to Non-Final Office Action dated Oct. 26, 2007, for U.S. Appl. No. 11/159,533, filed Jun. 23, 2005, 15 pages.
Amendment in Response to Non-Final Office Action dated Dec. 18, 2009, for U.S. Appl. No. 11/704,685, filed Feb. 9, 2007, 32 pages.
Amendment in Response to Non-Final Office Action dated Oct. 6, 2010, for U.S. Appl. No. 12/323,183, filed Nov. 25, 2008, 11 pages.
Amendment in Response to Non-Final Office Action dated Jan. 14, 2011, for U.S. Appl. No. 11/601,376, filed Nov. 17, 2006, 14 pages.
Amendment in Response to Non-Final Office Action dated Jan. 14, 2011, for U.S. Appl. No. 12/368,242, filed Feb. 9, 2009, 19 pages.
Amendment in Response to Non-Final Office Action dated Mar. 21, 2011, for U.S. Appl. No. 11/778,498, filed Jul. 16, 2007, 21 pages.
Extended European Search Report dated Jul. 26, 2010, for EP Patent Application No. 10166327.6, filed on Oct. 10, 2005, 6 pages.
Extended European Search Report dated Feb. 28, 2011, for EP Patent Application No. 11152879.0, filed on Oct. 10, 2006, 6 pages.
Extended European Search Report dated Mar. 2, 2011, for EP Patent Application No. 11152889.9, filed on Oct. 10, 2006, 6 pages.
Extended European Search Report dated Mar. 22, 2011, for EP Patent Application No. 11152743.7, filed on Feb. 9, 2007, 11 pages.
Final Office Action dated Feb. 7, 2008, for U.S. Appl. No. 11/159,533, filed Jun. 23, 2005, 8 pages.
Final Office Action dated Jan. 7, 2011, for U.S. Appl. No. 12/323,183, filed Nov. 25, 2008, 9 pages.
Final Office Action dated Jun. 9, 2011, for U.S. Appl. No. 12/513,491, filed Nov. 5, 2007 (Int'l. filing date), 10 pages.
Final Office Action dated Jun. 13, 2011, for U.S. Appl. No. 11/778,498, filed Jul. 16, 2007, 13 pages.
International Search Report dated Aug. 3, 2007, for PCT Application No. PCT/US2007/003582, filed on Feb. 9, 2007, 2 pages.
International Search Report dated Oct. 2, 2007, for PCT Application No. PCT/US05/36447, filed on Oct. 12, 2005, 1 page.
International Search Report dated Dec. 7, 2007, for PCT Application No. PCT/US2006/044766, filed on Nov. 17, 2006, 4 pages.
International Search Report dated May 20, 2009, for PCT Application No. PCT/US2007/083638, filed on Nov. 5, 2007, 5 pages.
International Search Report dated Jul. 8, 2009, for PCT Application No. PCT/US2008/054354, filed on Feb. 20, 2008, 8 pages.
International Search Report dated Aug. 4, 2008 for PCT Patent Application No. PCT/US2008/065666, filed on Jun. 3, 2008, 3 pages.
International Search Report dated Jun. 26, 2009, for PCT Application No. PCT/US2009/033596, filed on Feb. 9, 2009, 6 pages.
International Search Report dated Apr. 27, 2010, for PCT Patent Application No. PCT/US2010/026450, filed on Mar. 5, 2010, 1 page.
Non-Final Office Action dated Jul. 27, 2007, for U.S. Appl. No. 11/159,533, filed Jun. 23, 2005, 13 pages.
Non-Final Office Action dated Oct. 31, 2008, for U.S. Appl. No. 11/159,533, filed Jun. 23, 2005, 11 pages.
Non-Final Office Action dated Oct. 16, 2009, for U.S. Appl. No. 11/704,685, filed Feb. 9, 2007, 19 pages.
Non-Final Office Action dated Jul. 7, 2010, for U.S. Appl. No. 12/323,183, filed Nov. 25, 2008, 11 pages.
Non-Final Office Action dated Jul. 16, 2010, for U.S. Appl. No. 12/368,242, filed Feb. 9, 2009, 12 pages.
Non-Final Office Action dated Sep. 14, 2010, for U.S. Appl. No. 11/601,376, filed Nov. 17, 2006, 18 pages.
Non-Final Office Action dated Sep. 23, 2010, for U.S. Appl. No. 12/513,491, filed Nov. 5, 2007 (Int'l. filing date), 10 pages.
Non-Final Office Action dated Oct. 21, 2010, for U.S. Appl. No. 11/778,498, filed Jul. 16, 2007, 18 pages.
Non-Final Office Action dated Apr. 22, 2011, for U.S. Appl. No. 11/601,376, filed Nov. 17, 2006, 15 pages.
Non-Final Office Action dated Apr. 22, 2011, for U.S. Appl. No. 12/527,692, filed Feb. 20, 2008 (Int'l. filing date), 7 pages.
Notice of Allowance dated Apr. 23, 2010, for U.S. Appl. No. 11/704,685, filed Feb. 9, 2007, 10 pages.
Notice of Allowance dated Mar. 4, 2011, for U.S. Appl. No. 12/368,242, filed Feb. 9, 2009, 5 pages.
Response to Advisory Action dated Apr. 28, 2008, for U.S. Appl. No. 11/159,533, filed Jun. 23, 2005, 15 pages.
Response to Notice of Non-Compliant Amendment dated Nov. 2, 2007, for U.S. Appl. No. 11/159,533, filed Jun. 23, 2005, 7 pages.
Supplemental Response to Advisory Action dated Jun. 4, 2008, dated Jun. 9, 2008, for U.S. Appl. No. 11/159,533, filed Jun. 23, 2005, 15 pages.
Supplementary European Search Report dated Aug. 29, 2008, for EP Application No. 05803356.4, filed on Oct. 12, 2005, 7 pages.
Synthograft. (Date Unknown). "SynthoGraft Pure Phase Beta-Tricalcium Phosphate: The Next Generation of Regeneration," SynthoGraft Product Information Brochure, 6 pages.

(56) References Cited

OTHER PUBLICATIONS

Written Opinion of the International Searching Authority dated Aug. 3, 2007, for PCT Application No. PCT/US07/003582, filed on Feb. 8, 2007, 7 pages.
Written Opinion of the International Searching Authority dated Oct. 2, 2007, for PCT Application No. PCT/US05/36447, filed on Oct. 12, 2005, 4 pages.
Written Opinion of the International Searching Authority dated Dec. 7, 2007, for PCT Application No. PCT/US2006/044766 filed on Nov. 17, 2006, 6 pages.
Written Opinion of the International Searching Authority dated May 20, 2009, for PCT Application No. PCT/US2007/083638, filed on Nov. 5, 2007, 6 pages.
Written Opinion of the International Searching Authority dated Jul. 8, 2009, for PCT Application No. PCT/US2008/054354, filed on Feb. 20, 2008, 10 pages.
Written Opinion of the International Searching Authority dated on Aug. 4, 2008, for PCT Patent Application No. PCT/US2008/065666, filed on Jun. 3, 2008, 7 pages.
Written Opinion of the International Searching Authority dated Jun. 26, 2009, for PCT Patent Application No. PCT/US2009/033596, filed on Feb. 9, 2009, 6 pages.
Written Opinion of the International Searching Authority dated Apr. 27, 2010, for PCT Patent Application No. PCT/US2010/026450, filed on Mar. 5, 2010, 6 pages.
Amendment in Response to Non-Final Office Action dated Jul. 22, 2011, for U.S. Appl. No. 11/601,376, filed Nov. 17, 2006, 12 pages.
Al-Zube, L. et al. (2008). "Stimulation of Fracture Healing by Recombinant Human Platelet-Derived Growth Factor BB(rhPDGF-BB) Combined with Beta-Tricalcium Phosphate/Collagen Matrix in a Diabetic Rat Fracture Model," Poster No. 988, presented at 54$^{th}$ Annual Meeting of the Orthopaedic Research Society, San Francisco, CA, Mar. 2-5, 2008, one page.
Dines, J. et al. (2008). "rhPDGF-BB Enhances Rotator Cuff Tendon Healing in a Sheep Model," Paper No. 316, presented at 54$^{th}$ Annual Meeting of the Orthopaedic Research Society, San Francisco, CA, Mar. 2-5, 2008, one page.
Ehrlich, M.G. et al. (2008). "rhPDGF-BB Augmentation of New Bone Formation in a Rat Model of Distraction Osteogenesis," Poster No. 876, presented at 54$^{th}$ Annual Meeting of the Orthopaedic Research Society, San Francisco, CA, Mar. 2-5, 2008, one page.
Hollinger, J.O. (2007). "Enhanced Fracture Healing in the Geriatric-Osteoporotic Rat with Recombinant Human Platelet-Derived Growth Factor Homodimer BB (rhPDGF-BB) and Collagen/β-Tricalcium Phosphate Matrix," Poster No. 0930, 53rd Annual Meeting of the Orhopaedic Research Society, San Diego, CA, located at <http://www.ors.org/web/Transactions/53/0930.PDF>, last visited on Mar. 22, 2011, 1 page.
Kovacevic, D. et al. (2008). "PDGF Induces Cell Proliferation and Angiogenesis in a Rat Rotator Cuff Repair Model of Tendon-Bone Healing," Poster No. 1498, presented at 54$^{th}$ Annual Meeting of the Orthopaedic Research Society, San Francisco, CA, Mar. 2-5, 2008, one page.
Liu, Y. et al. (2008). "Evaluation of Recombinant Human Platelet-Derived Growth Factor-BB Combined with a Collagen Matrix as a Devices for Tendon Repair," Poster No. 1479, presented at 54$^{th}$ Annual Meeting of the Orthopaedic Research Society, San Francisco, CA, Mar. 2-5, 2008, one page.
Liu, Y. et al. (2009). "Evaluation of Four Collagen Matrices in Combination with Recombinant Human Platelet-Derived Growth Factor-BB (rhPDGF-BB) for Application in Rotator Cuff Repair," Poster No. 1266, presented at 55$^{th}$ Annual Meeting of the Orthopaedic Research Society, Las Vegas, NV, Feb. 22-25, 2009, one page.
Perrien, D.S. et al. (2008). "Percutaneous Injection of GEMOS® 2, a Cobmination of rhPDGF-BB and Bovine Type I Collagen/β Tricalcium Phosphate (βTCP) Matrix Increases Vertebral Bone Mineral Density in Geriatric Female Baboons," Poster No. 963, 54$^{th}$ Annual Meeting of the Orthopaedic Research Society, San Francisco, CA, located at <http://www.ors.org/web/Transactions/54/0963.PDF>, last visited on Mar. 22, 2011, 1 page.
Young, C.S. et al. (2007). "Bone Toxicology Study of Recombinant Human Platelet-Derived Growth Factor-BB (rhPDGF-BB) Injected Locally at the Metatarsus and Femur of Rats," Poster No. 1550, 53$^{rd}$ Annual Meeting of the Orhopaedic Research Society, San Diego, CA, located at <http://www.ors.org/web/Transactions/53/1550.PDF>, last visited on Mar. 22, 2011, 1 page.
Young, C.S. et al. (2008). "Release, Potency and Stability of Clinical Formulation of Recombinant Human Platelet-Derived Growth Factor-BB (rhPDGF-BB) Combined with Two Osteoconductive Materials: GEM OS® 1 and GEM 21s®," Poster No. 1693, presented at 54$^{th}$ Annual Meeting of the Orthopaedic Research Society, San Francisco, CA, Mar. 2-5, 2008, one page.
Young, C.S. (2009). "Distribution, Mass Balance and Excretion of $^{125}$Iodine-Labeled Recombinant Human Platelet-Derived Growth Factor BB (rhPDGF-BB) Administered Intravenously to Rats," Poster No. 597, presented at 55$^{th}$ Annual Meeting of the Orthopaedic Research Society, Las Vegas, NV, Feb. 22-25, 2009, one page.

\* cited by examiner

COMPOSITIONS AND METHODS FOR TREATING BONE

CROSS-REFERENCE TO RELATED APPLICATIONS

This application is a continuation application of U.S. Ser. No. 11/704,685, filed Feb. 9, 2007, issued as U.S. Pat No. 7,799,754 on Sep. 21, 2010, which is a continuation-in-part application of U.S. Ser. No. 11/159,533, filed Jun. 23, 2005, issued as U.S. Pat No. 7,743,678 on Jan. 6, 2009,which is a continuation-in-part application of U.S. Ser. No. 10/965, 319, filed Oct. 14, 2004, now abandoned, which claims priority benefit to U.S. Provisional Patent Application No. 60/771,826, filed Feb. 9, 2006, U.S. Provisional Patent Application No. 60/817,988, filed Jun. 30, 2006 and U.S. Provisional Patent Application No. 60/859,809, filed Nov. 17, 2006, the entire contents of which are hereby incorporated by reference.

FIELD OF THE INVENTION

The present invention relates to compositions and methods for the treatment of bone, particularly impaired or damaged bone.

BACKGROUND OF THE INVENTION

Musculoskeletal problems are pervasive throughout the population in all age groups and in both sexes. Half of Americans will need services for fractures at some point in their lifetime according to a widely published article presented at the 2003 annual meeting of the American Academy of Orthopedic Surgeons (AAOS). More than $10 billion per year is spent in the U.S. on hospital care associated with fracture treatment according to this report.

Bone health is an increasingly important issue as over 25 million people suffer from osteoporosis and 7 million more experience bone fractures annually in the United States. Osteoporosis and poor bone health contribute significantly to impaired bone structure leading to facile bone fracture and compromised bone repair. According to the Society of Cardiovascular and Interventional Radiology, osteoporosis causes about 700,000 fractures of the vertebrae each year.

Many factors can contribute to poor bone health. Several factors are excessive alcohol consumption, smoking, poor diet, physical inactivity, and genetic predisposition. Moreover, aging and osteoporosis contribute to decreased bone mass and mineral density as well as decreased bone fracture healing rates. Potential contributory factors to decreased bone healing rates in osteoporotic individuals include a reduction in the maturation of osteoblast progenitor cells, reduction in proliferative osteoprogenitor cell activity, decrease in bone forming capacity of mature osteoblasts, reduced osteoblastic response to chemical signaling, and a negative imbalance between bone formation and bone resorption.

Healthy bone may be deleteriously affected by weakened bone or by compensatory mechanisms that affect the load on the healthy bone. A patient with an injury on one side of the body, for example a fractured hip or an impaired femur due to avascular necrosis or osteoarthritis, may favor the injured side and add load to the contralateral hip or femur. Within the vertebral column, a diseased vertebra may add stress to adjacent vertebrae above or below it, eventually causing damage to these vertebrae. What is needed is a method to strengthen these otherwise healthy bones that are subject to additional stress and potential damage in order to prevent or mitigate such damage.

Vertebral compression fractures (VCFs) are the most common osteoporotic fractures, occurring in about 20% of post-menopausal women (Eastell et al., *J Bone Miner Res* 1991; 6:207-215). It is estimated that 700,000 VCFs occur annually, and only 250,000 of these are diagnosed and treated. Because these fractures are left untreated, osteoporosis may remain untreated and progress rapidly. Postmenopausal women have a 5-fold increased risk of sustaining another vertebral fracture within the coming year and 2-fold increased risk of other fragility fractures, including hip fractures (Klotzbuecher et al, *J Bone Miner Res,* 2000; 15:721-739).

VCFs occur when there is a break in one or both of the vertebral body end plates, usually due to trauma, causing failure of the anterior column and weakening the vertebrae from supporting the body during activities of daily living. Vertebral compression fractures caused by osteoporosis can cause debilitating back pain, spinal deformity, and height loss. Both symptomatic and asymptomatic vertebral fractures are associated with increased morbidity and mortality. With the number of aged people at risk for osteoporosis is expected to increase dramatically in the coming decades, accurate identification of VCFs and treatment intervention is necessary to reduce the enormous potential impact of this disease on patients and health care systems.

Traditionally, VCFs caused by osteoporosis have been treated with bed rest, narcotic analgesics, braces, and physical therapy. Bed rest, however, leads to accelerated bone loss and physical deconditioning, further aggravating the patient as well as contributing to the problem of osteoporosis. Moreover, the use of narcotics can worsen the mood and mentation problem that may already be prevalent in the elderly. Additionally, brace wear is not well-tolerated by the elderly. Although the current treatments of osteoporosis such as hormone replacement, bisphosphonates, calcitonin, and parathyroid hormone (PTH) analogs deal with long-term issues, except for calcitonin, they provide no immediate benefit in terms of pain control once a fracture occurs (Kapuscinski et al., *Master Med. Pol.* 1996; 28:83-86).

Recently, minimally invasive treatments for vertebral body compression fractures, vertebroplasty and kyphoplasty, have been developed to address the issues of pain and fracture stabilization. Vertebroplasty is the filling of a fractured vertebral body with the goals of stabilizing the bone, preventing further collapse, and eliminating acute fracture pain. Vertebroplasty, however, does not attempt to restore vertebral height and/or sagittal alignment. In addition, because there is no void in the bone, vertebral filling is performed under less control with less viscous cement and, as a consequence, filler leaks are common.

Kyphoplasty is a minimally invasive surgical procedure with the goal of safety, improving vertebral height and stabilizing VCF. Guided by x-ray images, an inflatable bone tamp is inflated in the fractured vertebral body. This compacts the inner cancellous bone as it pushes the fractured cortices back toward their normal position. Fixation can then be done by filling the void with a biomaterial under volume control with a more viscous cement. Although kyphoplasty is considered a safe and effective treatment of vertebral compression fractures, biomechanical studies demonstrate that cement augmentation places additional stress on adjacent levels. In fact, this increased stiffness can decrease the ultimate load to failure of adjacent vertebrae by 8 to 30% and provoke subsequent fractures (Berlemann et al., *J Bone*

Joint Surgery BR, 2002; 84:748-52). Compression fracture of one or more vertebral bodies subsequent to vertebroplasty or kyphoplasty is referred to herein as a "secondary vertebral compression fracture."

In a recent clinical study, a higher rate of secondary vertebral compression fracture was observed after kyphoplasty compared with historical data for untreated fractures. Most of these occurred at an adjacent level within 2 months of the index procedure. After this two-month period, there were only occasional secondary vertebral compression fractures which occurred at remote levels. This study confirmed biomechanical studies showing that cement augmentation places additional stress on adjacent level. (Fribourg et al., Incidence of subsequent vertebral fracture after kyphoplasty, *Spine,* 2004; 20; 2270-76).

Given the increased incidence of the use of minimally invasive surgical techniques for the treatment of vertebral compression fractures, and the predisposition of adjacent vertebrae to undergo secondary compression fracture, an unmet clinical need exists to prophylactically treat and prevent secondary VCFs.

Fractures of the distal radius are an important public-health problem and a major source of morbidity in the elderly. An estimated 1.4 million hand and forearm wrist fractures occur annually, and of these, nearly half (44%) are fractures of the ulna and radius. In the United States, 17% of all emergency room visits are due to wrist injuries [Hanel et al., *Orthop. Clin. North Am.* Jan. 33(1): 35-57 2002]. Distal radius fractures account for one sixth of all fractures seen in the emergency department (McMurtry et al., *Fractures of the Distal Radius,* 1992). Nearly one in four women will sustain a fracture of the distal radius by age 90, resulting in approximately 200,000 fractures annually in the United States with an estimated direct cost of nearly $150 million (Phillips et al., *Bone* 1988, 9:271-9, 1986). Further, because they occur most often in post-menopausal, osteoporotic women, these women have diminished bone density, which makes their fractures particularly troublesome to treat and susceptible to re-fracture.

Currently, there is no consensus on the preferred treatment of distal radius fractures. Typically, stable fractures receive closed reduction and immobilization in a plaster cast. Unstable distal radius fractures, however, may be treated with percutaneous pins incorporated in a plaster cast, metal external skeletal-fixation with or without pins and/or bone graft, limited open reduction with or without bone grafting, or extensive open reduction and internal fixation with or without pins and/or bone graft.

Recent reports have demonstrated the ability of volar fixed-angle plates to provide more stable internal fixation for surgical procedures that require open reduction and internal fixation (ORIF), and decrease subsequent morbidity in the treatment of unstable distal radius fractures compared to other internal fixation techniques (Orbay et al., *J. Hand. Surg.* 29A, 96-102, 2004).

The surgical assessment to determine a treatment plan based on the various fracture morphologies can be complex. Treatment-based fracture classifications are often used to determine the optimal treatment and attempt to predict an outcome based on the fracture pattern. A clinically useful classification system should assist the surgeon to evaluate and describe the fracture pattern, help select a therapeutic modality to treat the fracture, and be prognostic of the clinical outcome. The universally accepted AO System is a detailed fracture classification organized in order of increasing severity for both the bony extra- and intra-articular involvements. Type A fractures are extra-articular fractures that do not invade the articulating surface(s); type B describes limited articular fractures; and type C involve complex articular fractures. Each type is further divided into three subgroups based on the morphological complexity, treatment difficulty, and clinical prognosis.

In some cases, distal radius fractures require bone graft to ensure adequate bone healing. One of the most widely used options for bone graft is autologous bone. There have been problems, however, associated with autograft, including disadvantages associated with autologous bone grafting. Most of these problems result from the harvest of the bone graft, including increased operative time, hospital stay, cost, increased blood loss, post-operative pain, risk of infection and/or fracture. Other complications associated with autograft include a potential nidus for infection associated with avascular bone, limited tissue supply, and variability in cellular activity of the bone graft (Younger et al., *J. Orthop. Trauma,* 3, 192-195, 1989). The morbidity associated with autograft demonstrates the need for a better alternative for a chemotactic, mitogenic, and angiogenic bone graft substitute as an alternative for fracture augmentation.

In view of the significant health issues presented by poor bone health and bone diseases, such as osteoporosis, it would be desirable to provide compositions operable to facilitate bone fracture healing processes and promote healthy bone remodeling activities. It would additionally be desirable to provide methods of treating fractured or otherwise impaired bone with compositions operable to promote fracture healing and healthy bone remodeling processes. In view of the difficulties associated with autologous bone grafts, it would be desirable to provide alternative osteogenic regeneration systems. It would additionally be desirable to provide alternative osteogenic regeneration systems in bone fracture treatments, including fractures of bones such as the distal radius and associated anatomical structures of the wrist.

SUMMARY

In accordance with embodiments of the present invention, there are provided compositions and methods for the treatment of bone, including impaired bone such as fractured bone, diseased bone, weakened bone, and bone susceptible to increased load, such as increased compensatory load. These compositions and methods facilitate bone formation and strengthen bone.

The compositions of the present invention are used to facilitate strengthening and healing of bone, including fractured bone. Any bone may be treated with the compositions of the present invention, including but not limited to the humerus, ulna, radius, femur, tibia, fibula, patella, ankle bones, wrist bones, carpals, metacarpals, phalanges, tarsals, metatarsals, ribs, sternum, vertebrae, scapula, clavicle, pelvis, sacrum and craniofacial bones. In specific embodiments, the radius, femur, tibia and one or more vertebrae are treated with the compositions and methods of the present invention.

In one aspect, a composition provided by the present invention for the treatment of bone comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. The concentration of PDGF within the solution may be within any of the concentration ranges stated above.

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as recombinant human PDGF-BB (rhPDGF-BB).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of intact rhPDGF-B (1-109).

A biocompatible matrix, according to some embodiments of the present invention, comprises a bone scaffolding material. In some embodiments, a bone scaffolding material comprises calcium phosphate. Calcium phosphate, in one embodiment, comprises β-tricalcium phosphate.

In another aspect, the present invention provides a composition for the treatment of bone comprising a PDGF solution disposed in a biocompatible matrix, wherein the biocompatible matrix comprises a bone scaffolding material and a biocompatible binder. The PDGF solution may have a concentration of PDGF as described above. A bone scaffolding material, in some embodiments, comprises calcium phosphate. In one embodiment, a calcium phosphate comprises a β-tricalcium phosphate. In one aspect, biocompatible matrices may include calcium phosphate particles with or without biocompatible binders or bone allograft such as demineralized freeze-dried bone allograft (DFDBA) or particulate demineralized bone matrix (DBM). In another aspect, biocompatible matrices may include bone allograft such as DFDBA or DBM.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises collagen, such as bovine or human collagen.

The present invention additionally provides methods for producing compositions for the treatment of bone as well as methods for treating bone. In one embodiment, a method for producing a composition comprises providing a solution comprising PDGF, providing a biocompatible matrix, and disposing the solution in the biocompatible matrix.

In another embodiment, a method for treating impaired bone comprises providing a composition comprising a PDGF solution disposed in a biocompatible matrix and applying the composition to impaired bone. In a further embodiment, a method for treating impaired bone comprises providing a composition comprising a PDGF solution disposed in a biocompatible matrix, disposing the composition in a syringe, and injecting the composition at a site of impaired bone.

The present invention additionally provides methods for producing compositions for use in the treatment of fractures. In one embodiment, a method for producing a composition comprises providing a solution comprising PDGF, providing a biocompatible matrix, and disposing the solution in the biocompatible matrix.

In another embodiment, a method for treating a fracture comprises providing a composition comprising a PDGF solution disposed in a biocompatible matrix and applying the composition to the fracture. In some embodiments, applying the composition comprises injecting the composition into the fracture. In one embodiment, injecting comprises percutaneous injection of the composition into the fracture site. In another embodiment, the composition is injected into an open or surgically exposed fracture. In a further embodiment, applying the composition comprises disposing the composition in the fracture with a spatula or other device.

In some embodiments, a method for treating a fracture further comprises reducing the fracture and/or stabilizing the fracture. Reducing the fracture, according to some embodiments, comprises open reduction. In other embodiments, reducing the fracture comprises closed reduction. Moreover, stabilizing a fracture, in some embodiments, comprises applying an external or internal fixation device to the fracture.

In another embodiment, a method for treating a fracture comprises accelerating new bone fill in the fracture, wherein accelerating comprises providing a composition comprising a PDGF solution disposed in a biocompatible matrix and applying the composition to the fracture.

In another aspect, the present invention provides a kit comprising a solution comprising PDGF in a first container and a second container comprising a biocompatible matrix. In some embodiments, the solution comprises a predetermined concentration of PDGF. The concentration of PDGF can be predetermined according to the nature or classification of the fracture being treated. The kit may further comprise a bone scaffolding material and the bone scaffolding material may further comprise a biocompatible binder. Moreover, the amount of biocompatible matrix provided by a kit can be dependent on the nature or classification of the bone being treated. Biocompatible matrix that may be included in the kit may be a bone scaffolding material, a bone scaffolding material and a biocompatible binder, and/or bone allograft such as demineralized freeze-dried bone allograft (DFDBA) or particulate demineralized bone matrix (DBM). In one embodiment the bone scaffolding material comprises a calcium phosphate, such as β-TCP. A syringe can facilitate disposition of the PDGF solution in the biocompatible matrix for application at a surgical site, such as a site of fracture in the bone. The kit may also contain instructions for use.

In another aspect, the present invention provides a composition for the treatment of bone comprising a PDGF solution disposed in a biocompatible matrix, wherein the biocompatible matrix comprises a bone scaffolding material and a biocompatible binder. The PDGF solution may have a concentration of PDGF as described above. A bone scaffolding material, in some embodiments, comprises calcium phosphate. In one embodiment, a calcium phosphate comprises a β-tricalcium phosphate. In one aspect, biocompatible matrices may include calcium phosphate particles with or without biocompatible binders or bone allograft such as demineralized freeze-dried bone allograft (DFDBA) or particulate demineralized bone matrix (DBM). In another aspect, biocompatible matrices may include bone allograft such as DFDBA or DBM.

In some embodiments of the present invention, compositions for promoting bone formation in vertebral bodies and compositions for preventing or reducing the likelihood of vertebral compression fractures further comprise at least one contrast agent. Contrast agents, according to embodiments of the present invention, are substances operable to at least partially provide differentiation of two or more bodily tissues when imaged. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)-N,N'-bis[2-hydroxy-1-(hydroxymethyl)-ethyl]-2,4,6-tri-iodo-5-lactamidoisophthalamide (Iopamidol) and derivatives thereof.

Accordingly, it is an object of the present invention to provide compositions comprising PDGF useful in facilitating and, in some embodiments, accelerating healing of fractures. It is another object of the present invention to provide a composition comprising PDGF disposed in a biocompatible matrix and methods of using such as composition as an alternative to autologous bone graft in the treatment of fractures.

Another object of the present invention to provide compositions comprising PDGF useful in strengthening bone.

Still another object of the present invention is to provide compositions comprising PDGF useful in strengthening weakened bone.

Yet another object of the present invention is to provide compositions comprising PDGF useful in strengthening bone subjected to compensatory shifts in weight bearing.

Yet another object of the present invention is to provide compositions comprising PDGF useful in strengthening bone weakened due to compensatory shifts in weight bearing, such as vertebrae adjacent to a damaged vertebra, or a femur contralateral to an injured femur or hip.

These and other embodiments of the present invention are described in greater detail in the detailed description which follows. These and other objects, features, and advantages of the present invention will become apparent after review of the following detailed description of the disclosed embodiments and claims.

DETAILED DESCRIPTION

Figure 1:
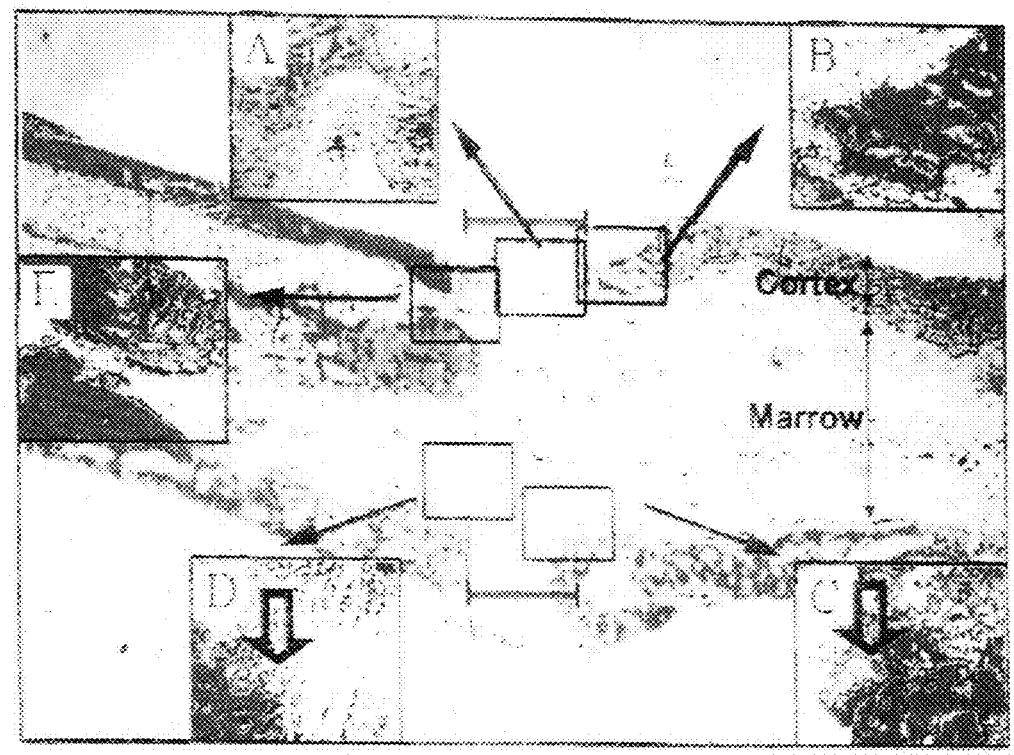
FIG. 1 displays photomicrographs of healing processes at an untreated site of bone fracture in an osteoporotic rat.

The present invention provides compositions and methods for the treatment of bone. Bone may be normal bone or impaired bone. Impaired bone, as used herein, comprises bone that is damaged, diseased, weakened, or otherwise functionally defective. Impaired bone, for example, can include fractured bone and low density bone resulting from any cause including but not limited to diseases such as osteoporosis, from use of corticosteroids or smoking. The present invention may also be employed for prophylactic treatment of bone that may be deleteriously affected by factors that may add stress on the bone or otherwise compromise the bone.

In one embodiment, the composition comprises a solution comprising PDGF and a biocompatible matrix, wherein the solution is disposed in the biocompatible matrix. In another embodiment, a composition comprises a PDGF solution disposed in a biocompatible matrix, wherein the biocompatible matrix comprises a bone scaffolding material and a biocompatible binder. In one aspect, biocompatible matrices may include calcium phosphate particles with or without biocompatible binders or bone allograft such as demineralized freeze-dried bone allograft (DFDBA) or particulate demineralized bone matrix (DBM). In another aspect, biocompatible matrices may DFDBA or particulate demineralized bone matrix DBM.

The compositions of the present invention are used to facilitate strengthening and healing of bone, including fractured bone. Any bone may be treated with the compositions of the present invention, including but not limited to the humerus, ulna, radius, femur, tibia, fibula, patella, ankle bones, wrist bones, carpals, metacarpals, phalanges, tarsals, metatarsals, ribs, sternum, vertebrae, scapula, clavicle, pelvis, sacrum and craniofacial bones. In specific embodiments, the radius, femur, tibia and vertebrae are treated with the compositions and methods of the present invention.

In one embodiment, the present invention provides compositions and methods for the treatment of fractures of the distal radius and related anatomical structures of the wrist. The present compositions and methods facilitate and, in some cases, accelerate the healing response in fractures of the distal radius, including bony union of the fracture site. In one embodiment, the compositions comprise a solution comprising PDGF and a biocompatible matrix, wherein the solution is disposed in the biocompatible matrix. In another embodiment, the compositions comprise a PDGF solution disposed in a biocompatible matrix, wherein the biocompatible matrix comprises a bone scaffolding material and a biocompatible binder. In another embodiment, the present invention provides compositions and methods for the treatment of fractures of tibia. In another embodiment, the present invention provides compositions and methods for the treatment of fractures of the vertebrae or for the strengthening of vertebrae adjacent to a damaged vertebra. According to embodiments described herein, the present invention provides compositions for promoting bone formation in a vertebral body and compositions for preventing or decreasing the likelihood of vertebral compression fractures, including secondary vertebral compression fractures.

Turning now to components that can be included in various embodiments of the present invention, compositions of the present invention comprise a solution comprising PDGF.

PDGF Solutions

PDGF plays an important role in regulating cell growth and division. PDGF, as with other growth factors, is operable to bind with the extracellular domains of receptor tyrosine kinases. The binding of PDGF to these transmembrane proteins switches on the kinase activity of their catalytic domains located on the cytosolic side of the membrane. By phosphorylating tyrosine residues of target proteins, the kinases induce a variety of cellular processes that include cell growth and extracellular matrix production.

In one aspect, a composition provided by the present invention comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; or about 1.0 mg/ml. It is to be understood that these concentrations are simply examples of particular embodiments, and that the concentration of PDGF may be within any of the concentration ranges stated above.

Various amounts of PDGF may be used in the compositions of the present invention. Amounts of PDGF that could be used include amounts in the following ranges: about 1 ug to about 50 mg, about 10 ug to about 25 mg, about 100 ug to about 10 mg, and about 250 ug to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, or any other assay known in the art for determining PDGF concentration. When provided herein, the molar concentration of PDGF is determined based on the molecular weight of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human PDGF, such as rhPDGF-BB.

PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthesis. When obtained from natural sources, PDGF can be derived from biological fluids. Biological fluids, according to some embodiments, can comprise any treated or untreated fluid associated with living organisms including blood.

Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available cGMP recombinant PDGF-BB can be obtained commercially from Chiron Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with one embodiment, the rhPDGF-BB comprises at least 65% of intact rhPDGF-B (1-109). In accordance with other preferred embodiments, the rhPDGF-BB comprises at least 75%, 80%, 85%, 90%, 95% or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethyl-piperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In a preferred embodiment, sodium acetate buffer is used. The buffers may be employed at different molarities, for example about 0.1 mM to about 100 mM, about 1 mM to about 50 mM, about 5 mM to about 40 mM, about 10 mM to about 30 mM, or about 15 mM to about 25 mM, or any molarity within these ranges. In one embodiment, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, more preferably about 5.5 to about 7.0, most preferably about 5.5 to about 6.5, or any value within these ranges. The pH of solutions comprising PDGF, in some embodiments, can be compatible with the prolonged stability and efficacy of PDGF or any other desired biologically active agent. PDGF is generally more stable in an acidic environment. Therefore, in accordance with one embodiment the present invention comprises an acidic storage formulation of a PDGF solution. In accordance with this embodiment, the PDGF solution preferably has a pH from about 3.0 to about 7.0, and more preferably from about 4.0 to about 6.5. The biological activity of PDGF, however, can be optimized in a solution having a neutral pH range. Therefore, in a further embodiment, the present invention comprises a neutral pH formulation of a PDGF solution. In accordance with this embodiment, the PDGF solution preferably has a pH from about 5.0 to about 8.0, more preferably about 5.5 to about 7.0, most preferably about 5.5 to about 6.5. In accordance with a method of the present invention, an acidic PDGF solution is reformulated to a neutral pH composition, wherein such composition is then used to treat fractures of the distal radius and related anatomical structures of the wrist to promote bone growth. In accordance with a preferred embodiment of the present invention, the PDGF utilized in the solutions is rhPDGF-BB.

In some embodiments, the pH of the PDGF containing solution may altered to optimize the binding kinetics of PDGF to a matrix substrate or linker. If desired, as the pH of the material equilibrates to adjacent material, the bound PDGF may become labile.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N, N,N',N'-tetraacetic acid (EGTA), aprotinin, ε-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to dispose the PDGF solutions and may also comprise a biocompatible binder either with or without a biocompatible matrix.

Biocompatible Matrix
Scaffolding Material

A biocompatible matrix, according to embodiments of the present invention, comprises a scaffolding material. The scaffolding material, according to embodiments of the present invention, provides the framework or scaffold for new tissue and/or bone growth to occur. A scaffolding material, in some embodiments, comprises at least one calcium phosphate. In other embodiments, a scaffolding material can comprise a plurality of calcium phosphates. Calcium phosphates suitable for use as a scaffolding material, in embodiments of the present invention, have a calcium to phosphorus atomic ratio ranging from 0.5 to 2.0. In some embodiments the biocompatible matrix comprises an allograft such as demineralized freeze-dried bone allograft (DFDBA) or particulate demineralized bone matrix (DBM).

Non-limiting examples of calcium phosphates suitable for use as scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-tricalcium phosphate, hydroxyapatite (OHAp), poorly crystalline hydroxyapatite, tetracalcium phosphate (TTCP), heptacalcium decaphosphate, calcium metaphosphate, calcium pyrophosphate dihydrate, carbonated calcium phosphate, and calcium pyrophosphate.

In some embodiments, a scaffolding material comprises porous structure. Porous scaffolding materials, according to some embodiments, can comprise pores having diameters ranging from about 1 µm to about 1 mm. In one embodiment, a scaffolding material comprises macropores having diameters ranging from about 100 µm to about 1 mm. In another embodiment, a scaffolding material comprises mesopores having diameters ranging from about 10 µm to about 100 µM. In a further embodiment, a scaffolding material comprises micropores having diameters less than about 10 µm. Embodiments of the present invention contemplate scaffolding materials comprising macropores, mesopores, and micropores or any combination thereof.

A porous scaffolding material, in one embodiment, has a porosity greater than about 25%. In another embodiment, a porous scaffolding material has a porosity greater than about 50%. In a further embodiment, a porous scaffolding material has a porosity greater than about 90%.

In some embodiments, a scaffolding material comprises a plurality of particles. A scaffolding material, for example, can comprise a plurality of calcium phosphate particles. Scaffolding particles, in one embodiment, have an average diameter ranging from about 1 μm to about 5 mm. In other embodiments, particles have an average diameter ranging from about 250 μm to about 750 μm. Scaffolding particles, in another embodiment, have an average diameter ranging from about 100 μm to about 400 μm. In a further embodiment, the particles have an average diameter ranging from about 75 μm to about 300 μm. In additional embodiments, scaffolding particles have an average diameter less than about 1 μm and, in some cases, greater than about 1 mm.

Scaffolding materials, according to some embodiments, can be provided in a shape suitable for implantation (e.g., a sphere, a cylinder, or a block). In other embodiments, scaffolding materials are moldable, extrudable and/or injectable. Moldable bone scaffolding materials can facilitate efficient placement of compositions of the present invention in and around target sites in bone. In some embodiments, moldable scaffolding materials are applied to bone with a spatula or equivalent device. In some embodiments, scaffolding materials are flowable. Flowable scaffolding materials, in some embodiments, can be applied to bone fractures through a syringe and needle or cannula. In some embodiments, the flowable scaffolding materials can be applied to the bone percutaneously. In other embodiments, flowable scaffolding materials can be applied to a surgically exposed bone fracture.

In some embodiments, scaffolding materials are bioresorbable. A scaffolding material, in one embodiment, can be resorbed within one year of in vivo implantation. In another embodiment, a scaffolding material can be resorbed within 1, 3, 6, or 9 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Scaffolding Comprising β-Tricalcium Phosphate

A scaffolding material for use as a biocompatible matrix, in some embodiments, comprises β-tricalcium phosphate (β-TCP). β-TCP, according to some embodiments, can comprise a porous structure having multidirectional and interconnected pores of varying diameters. In some embodiments, β-TCP comprises a plurality of pockets and non-interconnected pores of various diameters in addition to the interconnected pores. The porous structure of β-TCP, in one embodiment, comprises macropores having diameters ranging from about 100 μm to about 1 mm, mesopores having diameters ranging from about 10 μm to about 100 μm, and micropores having diameters less than about 10 μm. Macropores and micropores of the β-TCP can facilitate tissue in-growth including osteoinduction and osteoconduction while macropores, mesopores and micropores can permit fluid communication and nutrient transport to support tissue and bone regrowth, throughout the β-TCP biocompatible matrix.

In comprising a porous structure, β-TCP, in some embodiments, can have a porosity greater than 25%. In other embodiments, β-TCP can have a porosity greater than 50%. In a further embodiment, β-TCP can have a porosity greater than 90%.

In some embodiments, a scaffolding material comprises β-TCP particles. β-TCP particles, in one embodiment have an average diameter ranging from about 1 μm to about 5 mm. In other embodiments, β-TCP particles have an average diameter ranging from about 250 μm to about 750 μm. In another embodiment, β-TCP particles have an average diameter ranging from about 100 μm to about 400 μm. In a further embodiment, β-TCP particles have an average diameter ranging from about 75 μm to about 300 μm. In additional embodiments, β-TCP particles have an average diameter of sizes less than about 25 μm and, in some cases, sizes less than 1 μm.

A biocompatible matrix comprising a β-TCP scaffolding material, in some embodiments, is provided in a shape suitable for implantation (e.g., a sphere, a cylinder, or a block). In other embodiments, a β-TCP scaffolding material is moldable, extrudable, and/or flowable thereby facilitating application of the matrix to sites of fracture in the distal radius. Flowable matrices may be applied through syringes, tubes, or spatulas.

A β-TCP scaffolding material, according to some embodiments, is bioresorbable. In one embodiment, a β-TCP scaffolding material can be at least 75% resorbed one year subsequent to in vivo implantation. In another embodiment, a β-TCP scaffolding material can be greater than 90% resorbed one year subsequent to in vivo implantation.

Scaffolding Material and Biocompatible Binder

In another embodiment, a biocompatible matrix comprises a scaffolding material and a biocompatible binder.

Biocompatible binders, according to some embodiments, can comprise materials operable to promote cohesion between combined substances. A biocompatible binder, for example, can promote adhesion between particles of a scaffolding material in the formation of a biocompatible matrix. In certain embodiments, the same material may serve as both a scaffolding material and a binder if such material acts to promote cohesion between the combined substances and provides a framework for new tissue growth to occur, including bone growth.

Biocompatible binders, in some embodiments, can comprise collagen, elastin, polysaccharides, nucleic acids, carbohydrates, proteins, polypeptides, poly(α-hydroxy acids), poly(lactones), poly(amino acids), poly(anhydrides), polyurethanes, poly(orthoesters), poly(anhydride-co-imides), poly(orthocarbonates), poly(α-hydroxy alkanoates), poly (dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-polypropylene oxide) block copolymers, poly (ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, (β-cyclodextrin, γ-cyclodextrin, or sodium dextran sulfate), fibrin glue, lecithin, phosphatidylcholine derivatives, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, pluronic acids, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix.

A biocompatible matrix comprising a scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a scaffolding material and a biocompatible binder, in some embodiments, can also be provided in a predetermined shape including a block, sphere, or cylinder or any desired shape, for example a shape defined by a mold or a site of application.

A biocompatible matrix comprising a scaffolding material and a biocompatible binder, in some embodiments, is bioresorbable. A biocompatible matrix, in such embodiments, can be resorbed within one year of in vivo implantation. In another embodiment, a biocompatible matrix comprising a scaffolding material and a biocompatible binder can be resorbed within 1, 3, 6, or 9 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP scaffolding material and a biocompatible collagen binder. β-TCP scaffolding materials suitable for combination with a collagen binder are consistent with those provided hereinabove.

A collagen binder, in some embodiments, comprises any type of collagen, including Type I, Type II, and Type III collagens. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. In one embodiment, β-TCP particles suitable for combination with a collagen binder have an average diameter ranging from about 1 μm to about 5 mm. In another embodiment, β-TCP particles suitable for combination with a collagen binder have an average diameter ranging from about 1 μm to about 1 mm. In other embodiments, β-TCP particles have an average diameter ranging from about 200 μm to about 3 mm or about 200 μm to about 1 mm, or about 1 mm to about 2 mm. In some embodiments, β-TCP particles have an average diameter ranging from about 250 μm to about 750 μm. β-TCP particles, in other embodiments, have an average diameter ranging from about 100 μm to about 400 μm. In a further embodiment, β-TCP particles have an average diameter ranging from about 75 μm to about 300 μm. In additional embodiments, β-TCP particles have an average diameter less than about 25 μm and, in some cases, less than about 1 mm.

β-TCP particles, in some embodiments, can be adhered to one another by the collagen binder so as to produce a biocompatible matrix having a porous structure. In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm, mesopores having diameters ranging from about 10 μm to 100 μm, and micropores having diameters less than about 10 μm.

A biocompatible matrix comprising β-TCP particles and a collagen binder can have a porosity greater than about 25%. In another embodiment, the biocompatible matrix can have a porosity greater than about 50%. In a further embodiment, the biocompatible matrix can have a porosity greater than about 90%.

A biocompatible matrix comprising β-TCP particles, in some embodiments, can comprise a collagen binder in an amount ranging from about 5 weight percent to about 50 weight percent of the matrix. In other embodiments, a collagen binder can be present in an amount ranging from about 10 weight percent to about 40 weight percent of the biocompatible matrix. In another embodiment, a collagen binder can be present in an amount ranging from about 15 weight percent to about 35 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 75% resorbed one year subsequent to in vivo implantation. In another embodiment, a biocompatible matrix comprising β-TCP particles and a collagen binder can be greater than 90% resorbed one year subsequent to in vivo implantation.

In some embodiments, a solution comprising PDGF can be disposed in a biocompatible matrix to produce a composition for treating bone fractures, such as fractures of the distal radius and related anatomical structures of the wrist, or fractures of the tibia.

Disposing a PDGF Solution in a Biocompatible Matrix

In another aspect, the present invention provides methods for producing compositions for use in the treatment of distal radius fractures. In one embodiment, a method for producing such compositions comprises providing a solution comprising PDGF, providing a biocompatible matrix, and disposing the solution in the biocompatible matrix. PDGF solutions and biocompatible matrices suitable for combination are consistent with those described hereinabove.

In some embodiments, a PDGF solution can be disposed in a biocompatible matrix by soaking the biocompatible matrix in the PDGF solution. A PDGF solution, in another embodiment, can be disposed in a biocompatible matrix by injecting the biocompatible matrix with the PDGF solution. In some embodiments, injecting a PDGF solution can comprise disposing the PDGF solution in a syringe and expelling the PDGF solution into the biocompatible matrix to saturate the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can demonstrate a flowable paste or putty form prior to receiving a solution comprising PDGF.

Compositions Further Comprising Contrast Agents

In some embodiments, compositions comprising a PDGF solution disposed in a biocompatible matrix for treating bone or promoting bone formation, for example in a vertebral body, further comprise at least one contrast agent. Contrast agents, according to some embodiments, comprise cationic contrast agents, anionic contrast agents, nonionic contrast agents or mixtures thereof. In some embodiments, contrast agents comprise radiopaque contrast agents. Radiopaque contrast agents, in some embodiments, comprise iodo-compounds including (S)-N,N'-bis[2-hydroxy-1-(hydroxymethyl)-ethyl]-2,4,6-triiodo-5-lactamidoisophthalamide (Iopamidol) and derivatives thereof.

In some embodiments, methods of producing compositions for promoting bone formation in vertebral bodies and preventing or decreasing the likelihood of compression fractures in vertebral bodies further comprise providing at least one contrast agent and disposing the at least one contrast agent in the biocompatible matrix. In some embodiments, disposing at least one contrast agent in a biocompatible matrix comprises combining the at least one contrast agent with a PDGF solution and injecting the biocompatible matrix with the PDGF/contrast agent solution.

In another embodiment, disposing at least one contrast agent in a biocompatible matrix comprises combining the at least one contrast agent with a PDGF solution and soaking the biocompatible matrix in the PDGF/contrast agent solution. Alternatively, in some embodiments, a contrast agent is disposed in a biocompatible matrix independent of the PDGF solution.

Contrast agents, according to some embodiments of the present invention, facilitate placement or application of compositions of the present invention in and around vertebral bodies. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)-N, N'-bis[2-hydroxy-1-(hydroxymethyl)-ethyl]-2,4,6-triiodo-5-lactamidoisophthalamide (Iopamidol) and derivatives thereof.

Compositions Further Comprising Biologically Active Agents

Compositions of the present invention, according to some embodiments, can further comprise one or more biologically active agents in addition to PDGF. Biologically active agents that can be incorporated into compositions of the present invention, in addition to PDGF, can comprise organic molecules, inorganic materials, proteins, peptides, nucleic acids (e.g., genes, gene fragments, small-insert ribonucleic acids [si-RNAs] gene regulatory sequences, nuclear transcriptional factors, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). Preferred biologically active compounds that can be incorporated into compositions of the present invention include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, or calcitonin mimetics, statins, statin derivatives, fibroblast growth factors, insulin-like growth factors, growth-differentiating factors, and parathyroid hormone. Preferred factors also include protease inhibitors, as well as osteoporotic treatments that decrease bone resorption including bisphonates, and antibodies to NF-kB ligand (RANK) ligand.

Standard protocols and regimens for delivery of additional biologically active agents are known in the art. Additional biologically active agents can introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition of the present invention, according to some embodiments, can further comprise the addition of additional grafting materials with PDGF including autologous bone marrow, autologous platelet extracts, allografts, synthetic bone matrix materials, xenografts, and derivatives thereof.

Methods of Treating Bone

The present invention also provides methods of treating bone, including impaired bone. In one embodiment, a method for treating bone comprises providing a composition comprising a PDGF solution disposed in a biocompatible matrix and applying the composition to bone. In some embodiments, applying the composition to impaired bone can comprise molding the composition to the contours of the impaired bone. A composition, for example, can be molded into a bone fracture site thereby filling the volume created by the fracture.

A method for treating bone, in another embodiment, comprises providing a composition comprising a PDGF solution disposed in a biocompatible matrix, disposing the composition in a syringe, and injecting the composition at a site of impaired bone. In one embodiment, a composition comprising PDGF disposed in a biocompatible matrix can be injected into the volume created by a bone fracture. Injecting the composition, in some embodiments, can comprise penetrating tissue surrounding or covering a site of impaired bone with the syringe and depositing the composition at the site of impaired bone. In one embodiment, for example, a syringe can penetrate the skin and underlying tissue, such as muscle, covering a bone fracture site and subsequently deposit a composition of the present invention in and around the fracture. In such an embodiment, invasive techniques used to expose the fracture site for treatment, such as incisions and tissue removal, can be minimized. In another embodiment, a vertebral body may be injected with a composition comprising PDGF disposed in a biocompatible matrix, for example in an individual with osteoporosis.

The PDGF compositions of the present invention are used to facilitate healing of bone, including bone fractures. Any bone may be treated with the compositions of the present invention, including but not limited to the humerus, ulna, radius, femur, tibia, fibula, patella, ankle bones, wrist bones, carpals, metacarpals, phalanges, tarsals, metatarsals, ribs, sternum, vertebrae, scapula, clavicle, pelvis, sacrum and craniofacial bones.

In one embodiment, the PDGF compositions of the present invention may be applied directly to fractured bone. In another embodiment, the PDGF compositions of the present invention may be applied to hardware used to facilitate fracture stabilization, for example, intramedullary nails, screws and other hardware used by a physician of ordinary skill in the art, such as an orthopedic surgeon. In another embodiment, the PDGF compositions may be applied to openings in bone, such as sites of evulsion fractures, holes for screws, holes to receive intramedullary nails, or to the medullary canal.

PDGF solutions and biocompatible matrices suitable for use in compositions for the treatment of impaired bone according to embodiments of the present invention are consistent with those provided hereinabove.

Methods of Treating Fractures of the Distal Radius

The present invention provides compositions and methods for the treatment of fractures of bones, including the radius, particularly the distal radius and associated anatomical structures of the wrist. The present compositions and methods facilitate and, in some embodiments, accelerate the healing response in fractures of the distal radius, including bony union of the fracture site. Fractures of the distal radius, according to embodiments of the present invention, comprise all fracture types, including intra-articular and extra-articular fractures, as described by the AO classification system of distal radius fractures.

In one embodiment, distal radius fractures treated with compositions and methods of the present invention comprise all types of fractures as described by the AO classification of distal radius fractures. In some embodiments, a distal radius fracture comprises a Type A fracture (extra-articular). In other embodiments, a distal radius fracture comprises a Type B fracture (partial articular). In another embodiment, a distal radius fracture comprises a Type C1 fracture (complete articular, simple articular and metaphyseal fracture). In a further embodiment, a distal radius fracture comprises a Type C2 fracture (complete articular, simple articular with complex metaphyseal fracture). In some embodiments, a distal radius fracture comprises a Type C3 fracture (complete articular, complex articular and metaphyseal fracture).

In another embodiment, a method for treating a fracture of the distal radius comprises providing a composition comprising a PDGF solution disposed in a biocompatible matrix and applying the composition to a fracture in the distal radius. In some embodiments, applying the composition comprises injecting the composition into the fracture of the distal radius. In one embodiment, injecting comprises percutaneous injection of the composition into the fracture site. In another embodiment, the composition is injected into an open or surgically exposed fracture of the distal radius. In a further embodiment, applying comprises disposing the composition in the fracture with a spatula or other device. In one embodiment, contrast agents are optionally combined with the compositions of the present invention in order to facilitate visualization of the applied or injected composition.

In some embodiments, a method for treating a fracture of the distal radius further comprises reducing the fracture and/or stabilizing the fracture. Reducing the fracture, according to some embodiments, comprises open reduction. In other embodiments, reducing the fracture comprises closed reduction. Moreover, stabilizing the distal radius fracture, in some embodiments, comprises applying an external or internal fixation device to the fracture, such as a volar plate.

In another embodiment, a method for treating a fracture of the distal radius comprises accelerating new bone fill in the fracture, wherein accelerating comprises providing a composition comprising a PDGF solution disposed in a biocompatible matrix and applying the composition to the fracture.

In some embodiments, methods for treating fractures of the distal radius and associated anatomical structures of the wrist further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, such as vitamin $D_3$, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a fracture of the distal radius. In other embodiments, the at least one pharmaceutical composition is administered systemically to a patient. In one embodiment, for example, the at least one pharmaceutical composition is administered orally to a patient. In another embodiment, the at least one pharmaceutical composition is administered intravenously to a patient.

Methods of Treating Vertebral Bodies

The present invention provides compositions and methods useful for treating structures of the vertebral column, including vertebral bodies. In some embodiments of the present invention compositions are provided for promoting bone formation in a vertebral body. In other embodiments, compositions and methods are provided for preventing or decreasing the likelihood of vertebral compression fractures. In another embodiment, methods and compositions are provided for preventing or decreasing the likelihood of secondary vertebral compression fractures associated with vertebroplasty and kyphoplasty. The present compositions and methods are useful in treating vertebral bodies of patients with osteoporosis.

In another aspect, the present invention provides methods for promoting bone formation in a vertebral body comprising providing a composition comprising a PDGF solution disposed in a biocompatible matrix and applying the composition to at least one vertebral body. Applying the composition to at least one vertebral body, in some embodiments, comprises injecting the composition into the at least one vertebral body. In some embodiments, the composition can be applied to a plurality of vertebral bodies. Applying the composition, in some embodiments, comprises injecting at least one vertebral body with the composition. Compositions of the present invention, in some embodiments, are injected into the cancellous bone of a vertebral body. Vertebral bodies, in some embodiments, comprise thoracic vertebral bodies, lumbar vertebral bodies, or combinations thereof. Vertebral bodies, in some embodiments, comprise cervical vertebral bodies, coccygeal vertebral bodies, the sacrum, or combinations thereof.

In another aspect, the present invention provides methods comprising preventing or decreasing the likelihood of vertebral compression fractures, including secondary vertebral compression fractures. Preventing or decreasing the likelihood of vertebral compression fractures, according to embodiments of the present invention comprises providing a composition comprising a PDGF solution disposed in a biocompatible matrix and applying the composition to at least one vertebral body. In some embodiments, applying the composition to at least one vertebral body comprises injecting the composition into the at least one vertebral body. In one embodiment, the composition is applied to a second vertebral body, in some instances an adjacent vertebral body, subsequent to a vertebroplasty or kyphoplasty of a first vertebral body. In some embodiments, a composition comprising a PDGF solution disposed in a biocompatible matrix is applied to at least one high risk vertebral body. "High risk vertebral bodies" (HVB), as used herein, refer to vertebral bodies of vertebrae T5 through T12 as well as L1 through L4, which are at the greatest risk of undergoing secondary vertebral compression fracture.

In some embodiments, methods for promoting bone formation in vertebral bodies and preventing or decreasing the likelihood of compression fractures of vertebral bodies further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a vertebral body. In other embodiments, the at least one pharmaceutical composition is administered systemically to a patient. In one embodiment, for example, the at least one pharmaceutical composition is administered orally to a patient. In another embodiment, the at least one pharmaceutical composition is administered intravenously to a patient.

In some embodiments, a composition of the present invention is applied to a second vertebral body subsequent to vertebroplasty or kyphoplasty of a first vertebral body. In some embodiments, the second vertebral body is adjacent to the first vertebral body. In other embodiments, the second vertebral body is not adjacent to the first vertebral body. In a further embodiment, a composition of the present invention is applied to a third vertebral body subsequent to vertebroplasty or kyphoplasty of a first vertebral body. In some embodiments, the third vertebral body is adjacent to the first vertebral body. In other embodiments, the third vertebral body is not adjacent to the first vertebral body. Embodiments of the present invention additionally contemplate application of compositions provided herein to a plurality of vertebral bodies, including high risk vertebral bodies, subsequent to vertebroplasty or kyphoplasty of a first vertebral body. It is to be understood that first, second, and third vertebral bodies, as used herein, do not refer to any specific position in the vertebral column as methods for inhibiting vertebral compression fractures, including secondary compression fractures, can be applied to all types of vertebral bodies including thoracic vertebral bodies, lumbar vertebral bodies, cervical vertebral bodies, coccygeal vertebral bodies, and the sacrum.

In some embodiments, methods for promoting bone formation in vertebral bodies and preventing or decreasing the likelihood of compression fractures of vertebral bodies further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, such as vitamin $D_3$, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a vertebral body. In other embodiments, the at least one pharmaceutical composition is administered systemically to a patient. In one embodiment, for example, the at least one pharmaceutical composition is administered orally to a patient. In another embodiment, the at least one pharmaceutical composition is administered intravenously to a patient.

Kits

In another aspect, the present invention provides a kit comprising a solution comprising PDGF in a first container and a second container comprising a biocompatible matrix. In some embodiments, the solution comprises a predetermined concentration of PDGF. The concentration of PDGF can be predetermined according to the nature or classification of the fracture being treated. The kit may further comprise a bone scaffolding material and the bone scaffolding material may further comprise a biocompatible binder. Moreover, the amount of biocompatible matrix provided by a kit can be dependent on the nature or classification of the bone being treated. Biocompatible matrix that may be included in the kit may be a bone scaffolding material, a bone scaffolding material and a biocompatible binder, and/or bone allograft such as demineralized freeze-dried bone allograft (DFDBA) or particulate demineralized bone matrix (DBM). In one embodiment the bone scaffolding material comprises a calcium phosphate, such as β-TCP. A syringe can facilitate disposition of the PDGF solution in the biocompatible matrix for application at a surgical site, such as a site of fracture in the bone. The kit may also contain instructions for use.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of a Composition Comprising a Solution of PDGF and a Biocompatible Matrix A composition comprising a solution of PDGF and a biocompatible matrix was prepared according to the following procedure.

A pre-weighed block of biocompatible matrix comprising β-TCP and collagen was obtained. The β-TCP comprised pure β-TCP particles having sizes ranging from about 75 μm to about 300 μm. The β-TCP particles were formulated with approximately 20% weight percent soluble bovine collagen binder. A B-TCP/collagen biocompatible matrix can be commercially obtained from Kensey Nash (Exton, Pa.).

A solution comprising rhPDGF-BB was obtained. rhPDGF-BB is commercially available from Chiron Corporation at a stock concentration of 10 mg/ml (i.e., Lot # QA2217) in a sodium acetate buffer. The rhPDGF-BB is produced in a yeast expression system by Chiron Corporation and is derived from the same production facility as the rhPDGF-BB that is utilized in the products REGRANEX, (J&J) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention.

A ratio of about 91 μl of rhPDGF-BB solution to about 100 mg dry weight of the β-TCP/collagen biocompatible matrix was used to produce the composition. The rhPDGF-BB solution was expelled on the biocompatible matrix with a syringe, and the resulting composition was blended and molded into a thin strand for insertion into a 1 cc tuberculin syringe for placement at a site of impaired bone.

EXAMPLE 2

Bone Fracture Healing with Compositions Comprising a Solution of PDGF and a Biocompatible Matrix In order to evaluate the efficacy of various compositions to treat and enhance impaired bone repair, a study was conducted using osteoporotic rats. The model used for the present study was designed to mimic bone fracture repair in postmenopausal women who are estrogen deficient and prone to osteoporotic fractures.

The present study was conducted at Carnegie Mellon University (CMU), Bone Tissue Engineering Center, Pittsburgh, Pa. The study was approved by the University of Pittsburgh IACUC per Approval No. 0106070, and the surgical studies were administered under the guidance of the Division of Laboratory Animal Resources (AAALAC approved) at the University of Pittsburgh.

Eighty (80) 1-2-year old female Sprague-Dawley rats weighing at least 200 g each were used in the study. The rats were obtained from Harlan (Indianapolis, Ind.). The rats were ovariectomized (surgical removal of the ovaries) at Hilltop Lab Animals, Inc. (Scottsdale, Pa.) to make the rats estrogen deficient.

For the ovariectomy, the animals were anesthetized with isofluorane, then shaved and prepared with alcohol in the lower thoracic and lumbar regions. A longitudinal, midline incision was made in the skin of the lower lumbar region, and a transverse muscle incision was made on both the right and left sides of the body wall directly over the ovarian fat, which was externalized through either incision. The uterine horn and the blood vessels leading to the ovaries were isolated by tying a suture around them. They, along with any attached fat were cut away, and the remainders of the uterine horn returned to the cavity.

The ovariectomized rats were housed at Hilltop Laboratories in individual stainless steel cages for up to 4 months for stabilization after ovariectomy. The rats were additionally put on a 30% reduced caloric diet to ensure osteopenia over the 4 month course of recovery. The ovariectomized rats were transferred to Carnegie Mellon University and remained on the restricted diet for approximately 25 weeks prior to an osteotomy procedure.

Subsequent to ovariectomy and diet, the rats were subjected to an osteotomy procedure to simulate a bone fracture. Using a semi-aseptic procedure, each rat was prepped on an operating room table with heating pad and draped. 75 mg/kg Ketaject ketamine and 5 mg/kg Xylaject xylazine (Phoenix Pharmaceutical, Inc., St. Joseph, Mo.) were injected IM as anesthesia. The soft-tissue overlying the tibiae and knee joint was sharply dissected. With the leg in extension, the patella ligament was lateralized, then under flexion, an access hole in the proximal metaphysis into the medullary canal was prepared using a surgical drill and physiological saline irrigation. A 0.7 mm Kirschner wire (K-wire) was cut to the appropriate length to be sized to the tibiae. K-wire was obtained from K-Medic (Northvale, N.J.) Lot # K11262 and used to mimic the use of an IM Rod in treating fracture human tibia.

Next, a transverse osteotomy was prepared in the upper 3rd of right tibial diaphysis with a reciprocating saw (cuff −0.2 mm). Under semi-aseptic conditions (e.g., thorough alcohol wipes of operating area), a reduction of the transverse fracture was achieved using the K-wire which was inserted through the access hole to the distal portion of the tibia. The rats were divided into four test groups for bone fracture healing evaluation as follows:

Fracture alone (Untreated)—rats in this group received no treatment, and the fracture produced by the osteotomy was allowed to heal naturally.

Fracture+matrix (Control)—rats in this group received treatment with a composition of β-TCP/collagen matrix and a sodium acetate buffer. The composition was prepared in accordance with that provided in Example 1 with the sodium acetate buffer serving as a substitute for the PDGF solution.

Fracture+matrix (Low Conc.)—rats in this group received treatment with a composition of β-TCP/collagen matrix and rhPDGF-BB solution. The composition was prepared in accordance with that provided in Example 1, and the concentration of rhPDGF-BB in the solution was 0.3 mg/ml.

Fracture+matrix (High Conc.)—rats in this group received treatment with a composition of β-TCP/collagen matrix and rhPDGF-BB solution. The composition was prepared in accordance with that provided in Example 1, and the concentration of rhPDGF-BB in the solution was 1.0 mg/ml.

For the three test groups that received the β-TCP matrix+/−the PDGF solution, 18 mm length×2 mm width of the matrix material was placed around the transverse osteotomy. For the "untreated" group, no matrix was applied to the surgical site. Following treatment, soft tissues were closed in layers with resorbable 4-0 vicryl sutures using a CE4 cutting needle. Unprotected weight-bearing was allowed, and the animals resumed normal activity after the surgeries.

Of the 80 animals in the experiment, 6 animals were excluded from the data analysis, 2 due to fracture complications resulting from inappropriate K-wire placement, 2 due to technical problems with biomechanical testing, and 2 due to death post-surgery. The two deaths appeared to result from the aggressive surgical procedure and the effects of the anesthesia. No deaths associated with any treatment occurred in the study.

The animals were monitored daily for any adverse reactions to the implanted material including: edema, redness, and weight loss. Evaluation was made for signs of distress and pain include lethargy, bristled appearance, whimpering, wincing, failure to thrive (decreased overall activity or decreased feeding), and/or overexcited generalized activity. There were no significant differences between the four treatment groups for weight gain or loss.

Each of the four test groups as defined above were divided into temporal periods of 3 weeks and 5 weeks. Rats in each of the test groups were assigned to a 3 week period or a 5 week period. The 3 and 5 week periods correspond to the time lapse between osteotomy/treatment and harvesting of tissue to evaluate bone healing.

At the time of sacrifice, either 3 or 5 weeks post surgery, the rats from the four test groups, were euthanized using $CO_2$. The tibiae, including contralateral uninjured tibiae, were harvested, K-wires were delicately removed, and radiographs of the fractures performed. Tibiae that were selected at random for Micro-CT analysis were fixed in 10% neutral buffered formalin. The specimens that were collected for Micro-CT analysis were processed following CT analysis for histology. The remainder of the harvested tibiae (fractured and unfractured) were wrapped in saline-soaked gauze and stored at −20° C. until torsional biomechanical analysis was conducted. Table 1 summarizes the experimental set-up provided above.

TABLE 1

Summary of Experimental Treatments

| Treatments | R, B | MC/H |
|---|---|---|
| 3 weeks | | |
| Untreated Fracture | 8 | 2 |
| Vehicle + buffer | 8 | 2 |
| PDGF 0.3 mg/ml | 8 | 2 |
| PDGF 1.0 mg/ml | 8 | |
| TOTAL + extra | 40 | |
| 5 weeks | | |
| Untreated Fracture | 8 | 2 |
| Vehicle + buffer | 8 | 2 |
| PDGF 0.3 mg/ml | 8 | 2 |
| PDGF 1.0 mg/ml | 8 | 2 |
| TOTAL + extra | 40 | |

R = Radiographs,
B = Biomechanical testing
MC = Micro-CT analysis,
H = Histology analysis Radiography: Radiographs were taken using a Faxitron (Model # 43855C, Wheeling, Ill.) at settings of 28 kilovolts, 0.3 milliamps, shelf 8, for 9 seconds. By placing the specimens on the same shelf number in the exposure chamber, a constant distance between the X-ray source and film (specimen) was obtained. The film used was Kodak X-Omat AR(XAR)-5 Film (Kodak, Rochester, N.Y.).

Micro-CT: Of the 10 animals in each study group, 2 were pre-designated for micro-CT analysis. The specimens were scanned on a pCT 40 (Scanco Medical, Zurich, Switzerland) scanner. A field of vision of 12.3 mm and 1024×1024 matrix size were used resulting in an isotropic voxel resolution of 12 µm. Images were collected from approximately 28 mm of the tibia (from the epiphysis to the tibio-fibula junction). The resulting scan time was approximately 6 hours/specimen. The 16-bit gray scale images were binarized, using an appropriate threshold value(s), for 3D display and visualization.

Torsional Biomechanical Testing: Of the 10 animals in each study group, 8 were pre-designated to be evaluated for biomechanical testing. The mechanical properties of the healing fractured tibiae were measured by a destructive torsional testing procedure using a SmartTest testing machine. The fractured bones, and contralateral unfractured bones, were removed from −20° C. and thawed at room temperature for 12 hours. The bones were moistened with saline prior to loading onto the jig. All bones were oriented alike in the testing machine. The distal and proximal epiphyses of the tibia were marked with a line to denote placement in the jig. Only the diaphysis of the tibia was visible once in the jig. Before and during testing procedures, the tibiae were kept moist with saline.

External rotational displacement was applied at a rate of 0.25 degrees per second until failure Torque and displacement data were recorded on an IBM-compatible computer using the WinTest software (Version 2.56, BOSE-Enduratec Systems Group, Minnetonka, Minn.). The torsional stiffness, and ultimate torque and degree of angulation were calculated. Ultimate torque and stiffness describe the mechanical behavior of the fractured and intact bones.

Histology: Of the 10 animals in each study group, 2 were pre-designated for histological assessment. These were the same two animals within each test group that were evaluated by micro-CT analysis. The protocol as described in Table 2 was used for processing the fractured bones for histology evaluation. The tissues were processed through increasing concentrations of ethanol (EtOH), infused with methylmethacrylate (MMA) and embedded using techniques known to one of ordinary skill in the art. The embedded blocks were sectioned, mounted and stained. The embedded blocks were trimmed, and thin sections taken along the long dimension of the fractured bone. The sections were mounted onto glass slides and stained with Goldner's trichrome. Photomicrographs were taken at various powers to aid in histological analysis.

Radiographical Analysis: Radiographs were taken to confirm the location of the fractures and the reproducibility of injury between groups. Due to the presence of the β-TCP present at the fracture site, the radiographs were found to be of limited value for analyzing fracture healing.

Histological Analysis: Representative photomicrographs of fracture sites are provided for the 5 week time point for each of the four treatment groups. FIG. 1 displays photomicrographs of an untreated bone fracture site in an osteoporotic rat (Untreated). As shown in the micrographs, bone healing in the untreated site was not apparent across the osteotomy. The fracture site is identified by red bars. As a consequence of remodeling and minimal callus formation and healing, osteotomy widths across the cortices were unequal. There was a loose array of fibrous tissue admixed with granulation tissue elements and a mild inflammatory infiltrate as shown in FIGS. 1(a) and (d). Fracture margins in FIGS. 1(b)-(e) had minimal to no callus formation. There was, however, occasional evidence of a chondrogenic response at osteotomy margins as displayed in FIGS. 1(c) and (d).

Figure 2:
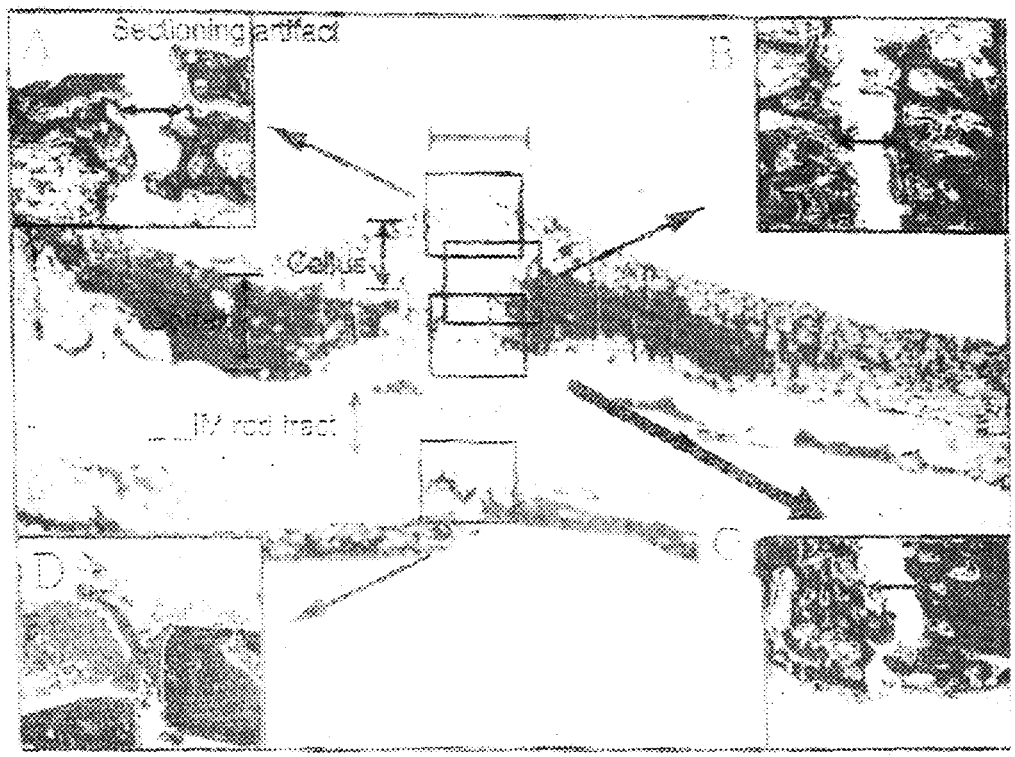
FIG. 2 displays photomicrographs of healing processes at a site of bone fracture in an osteoporotic rat treated with a bone scaffolding material.

FIG. 2 displays photomicrographs of healing processes at a site of bone fracture in an osteoporotic rat treated with β-TCP/collagen matrix and buffer (control). Bone healing and callus formation were scanty across and contiguous to the osteotomy. The fracture (osteotomy) margins were aligned and little periosteal callus was observed and appeared mostly on one cortex. As shown in FIGS. 2(a)-(c), the bridged callus had a small gap that may have occurred during histological sectioning. There was evidence of hemorrhage without callus formation as displayed in FIG. 2(d). The marrow was replaced by fibrous tissue that was moderately to markedly infiltrated by inflammatory cells.

Figure 3:
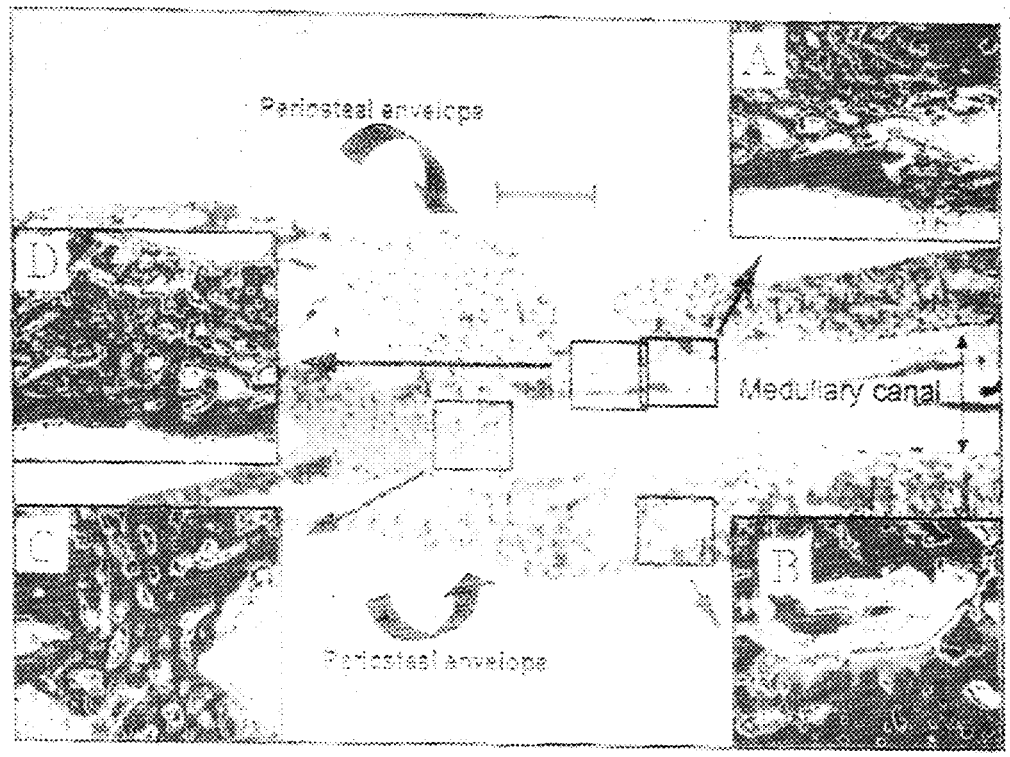
FIG. 3 displays photomicrographs of healing processes at a site of bone fracture in an osteoporotic rat treated with a composition comprising a PDGF solution and a biocompatible matrix according to an embodiment of the present invention.

FIG. 3 displays photomicrographs of healing processes at a site of bone fracture in an osteoporotic rat treated with a composition comprising a PDGF solution (0.3 mg/ml) and μ-TCP/collagen matrix (Low conc.). As shown in the micrographs, there was both woven and lamellar bone formation across the fracture (osteotomy). Also present was callus bridging both cortices and joining across the medullary canal indicating active bone healing and remodeling as evidenced by FIGS. 3(a), (c), and (d). Minimal loose fibrous-like connective tissue and inflammation was present in the medullary canal and along the intramedullary (IM) insertion rod. There was neither ectopic bone formation outside the periosteal envelope (curved arrows) nor inappropriate dense connective tissue fibrosis in the treatment area.

Figure 4:
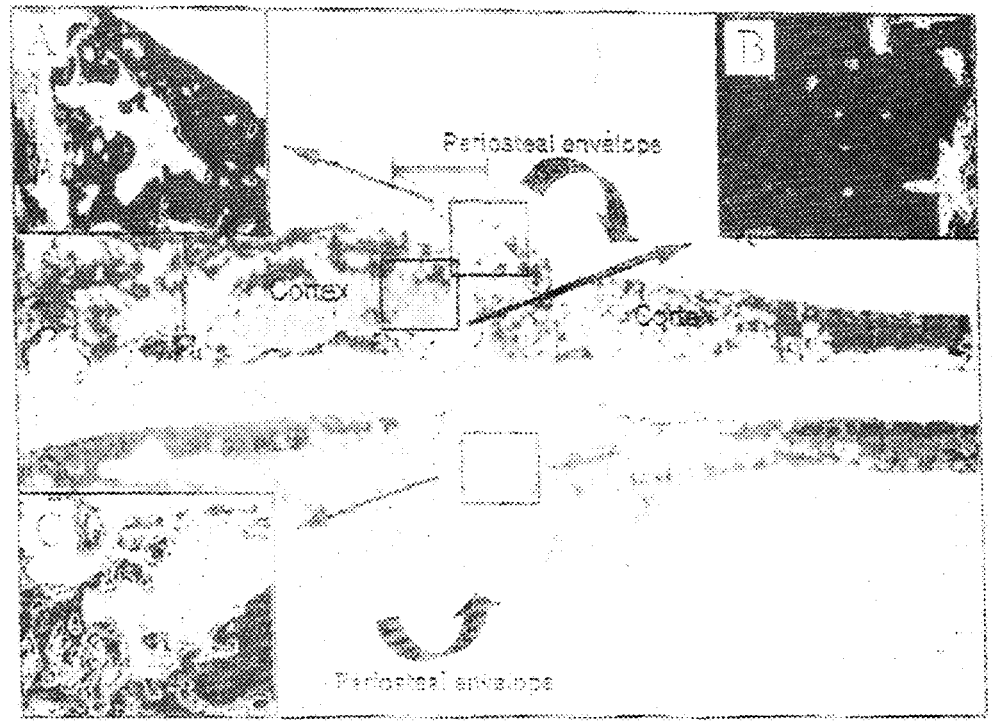
FIG. 4 displays photomicrographs of healing processes at a site of bone fracture in an osteoporotic rat treated with a composition comprising a PDGF solution and a biocompatible matrix according to an embodiment of the present invention.

FIG. 4 displays photomicrographs of healing processes at a site of bone fracture in an osteoporotic rat treated with a composition comprising a PDGF solution (1.0 mg/ml) and μ-TCP/collagen matrix (High conc.). New bone and remodeling was confined and localized to the fracture healing site, with lamellar bone formation. The fracture (osteotomy) margins were well aligned. FIGS. 4(a) and (c) display moderate to marked callus at the cortical margins with complete bridging in the lower cortex. There was slight loose connective tissue fibrosis in the medullary canal with minimal inflammatory infiltration. Consistent with the observations at the low concentration of PDGF, there was neither evidence of ectopic bone formation outside the periosteal envelope (curved arrows) nor undesired dense connective tissue fibrosis in the treatment area.

Figure 5:
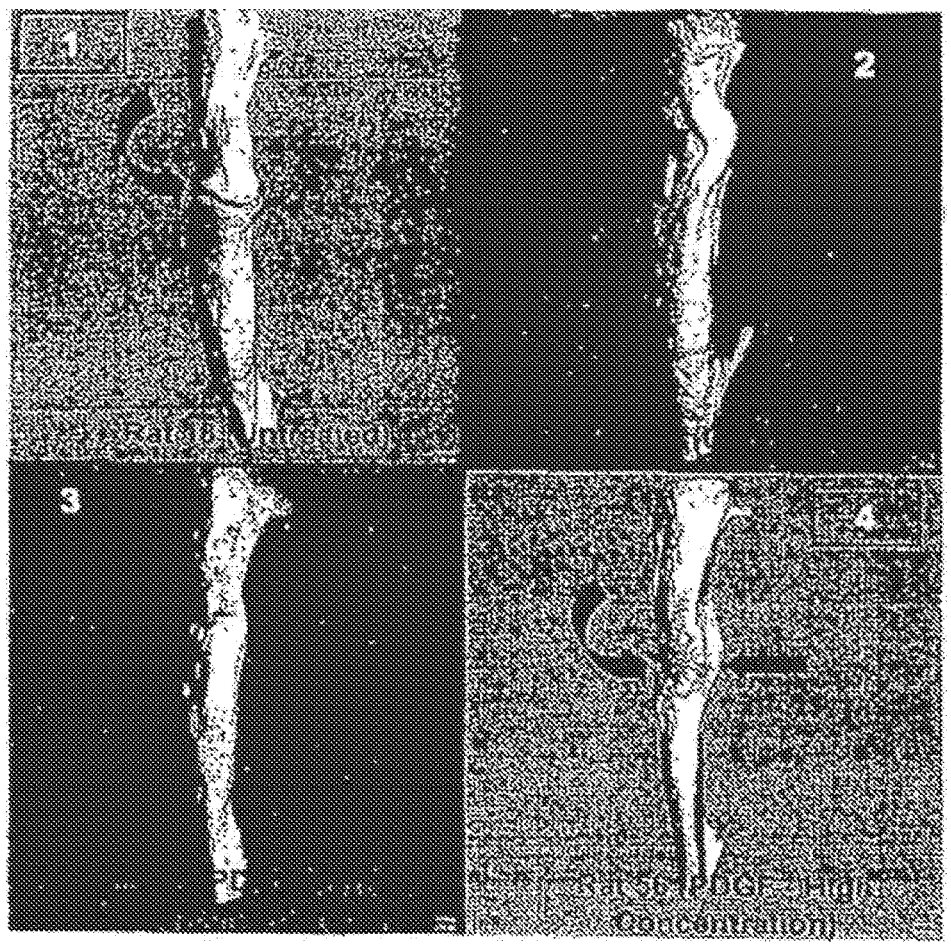
FIG. 5 displays micro-computer tomography (micro-CT) images of treated and untreated sites of bone fracture in osteoporotic rats according to embodiments of the present invention.

Micro-CT Analysis: Micro-CT (computer tomography) analysis was conducted on each of the four treatment groups at both the 3 and 5 week time points. Representative examples of the Micro-CT analysis for each of the four treatment groups at 5 weeks following injury are presented in FIG. 5. The results of the analysis demonstrated that there was evidence of the β-TCP particles remaining around the fracture sites at both the 3 and 5 week time points, though the amount present at 5 weeks was decreased from the 3 week time point. At neither of the two time points was there evidence of ectopic calcification in soft tissues. Overall, the microCT appearance of the healing fractures treated with the low and high concentrations of PDGF revealed that the process of bone fracture healing was normal and confined to the fracture site.

Biomechanical Testing Analysis: Biomechanical testing was conducted to measure fracture site strength for the four study groups, at both the 3 and 5 week time points. Both the fractured and contralateral unfractured legs were harvested from each animal with both legs evaluated for biomechanical strength in a torsion analysis. Torsion analysis was conducted using a SmartTest Servo Pneumatic Axial Torsional System, BOSE-EnduraTEC Systems Group, Minnetonka, Minn. with WinTest Software, Version 2.56.

Analysis of the contralateral unfractured leg allowed for direct comparison of the leg strength between the fracture and unfractured legs, as well as the establishment of a ratio of the torsion strength between the fractured and unfractured leg. The use of a ratio of leg strength within each animal allowed each animal to act as its own control in the data analysis, minimizing any differences that may have been present between animals such as age, size or effect of the ovariectomy procedure.

A summary of the biomechanical testing results for the torsion leg strength for the fractured leg and unfractured contralateral leg for the four treatment groups at the two time points is presented in Table 2. Statistical assessment of the data presented in Table 2 is presented in Tables 6-8. A summary of the torsion strength as a ratio of the fractured to unfractured leg within each animal is presented for the two time points in Tables 3 and 4.

TABLE 2

Comparison of Biomechanical Strength Testing

| Temporal Group (weeks) | Treatment | Dose PDGF (mg/mL) | Torque at Failure (Nm) | |
|---|---|---|---|---|
| | | | Fractured Leg | Unfractured Leg |
| 3 | Fracture alone (Untreated) | 0 | 0.0565 | 0.1215 |
| | Fracture + matrix (Control) | 0 | 0.0505 | 0.1176 |
| | Fracture + matrix/low dose PDGF (Low Conc.) | 0.3 | 0.0395 | 0.1026 |
| | Fracture + matrix/high dose PDGF (High Conc.) | 1.0 | 0.0475 | 0.1207 |
| 5 | Fracture alone (Untreated) | 0 | 0.0555 | 0.1152 |
| | Fracture + matrix (Control) | 0 | 0.0652 | 0.1048 |
| | Fracture + matrix/low dose PDGF (Low Conc.) | 0.3 | 0.0862 | 0.1117 |
| | Fracture + matrix/high dose PDGF (High Conc.) | 1.0 | 0.0854 | 0.1153 |

TABLE 3

Summary of Biomechanical Testing for all 4 Study Groups at 3 Weeks

| Strength ratio | Frx alone | Frx + matrix | Frx + Low | Frx + High |
|---|---|---|---|---|
| N | 6 | 8 | 8 | 7 |
| Mean* | 0.51 | 0.45 | 0.38 | 0.38 |
| Median* | 0.41 | 0.52 | 0.30 | 0.47 |
| Standard Deviation | 0.32 | 0.31 | 0.23 | 0.27 |
| Min-Max | 0.22-1.08 | 0-0.81 | 0.18-0.81 | 0-0.64 |

*The data is presented as the ratio of the torsion strength of the fractured leg to the contralateral unfractured leg. The ratio was calculated for each animal individually then pooled to obtain a mean value. A ratio of 1.0 would indicate that the fractured leg has equal torsional strength to the unfractured leg.

TABLE 4

Summary of Biomechanical Testing for all 4 Study Groups at 5 Weeks

| Strength ratio | Frx alone | Frx + matrix | Frx + Low | Frx + High |
|---|---|---|---|---|
| N | 7 | 8 | 7 | 7 |
| Mean* | 0.49 | 0.66 | 0.79 | 0.74 |
| Median* | 0.44 | 0.58 | 0.83 | 0.93 |
| Standard Deviation | 0.38 | 0.42 | 0.37 | 0.38 |
| Min-Max | 0-1.19 | 0-1.45 | 0.20-1.19 | 0-1.06 |

*The data is presented as the ratio of the torsion strength of the fractured leg to the contralateral unfractured leg. The ratio was calculated for each animal individually then pooled to obtain a mean value. A ratio of 1.0 would indicate that the fractured leg has equal torsional strength to the unfractured leg.

Assessment of the effect of time on the ratio of the torsion strength of the fractured leg to the unfractured leg was measured, with the results presented in Table 5. Table 5 demonstrates that for the untreated group there was no significant difference in the ratio observed between the 3 and 5 week time points. Similarly, for the β-TCP matrix treated animals (Control Group) there was no significant difference in the torsion strength ratio between the 3 and 5 week time points.

TABLE 5

Assessment of Time Effect for the Four Treatment Groups

| Treatment Group | Week 3 Mean Ratio | Week 5 Mean Ratio | One-Tailed P-Value* |
|---|---|---|---|
| Untreated | 0.51 | 0.49 | 0.4560 |
| Control | 0.45 | 0.66 | 0.1381 |
| Low Concentration | 0.38 | 0.79 | 0.0106 |
| High Concentration | 0.38 | 0.74 | 0.0296 |

*P-Value results from a two-sample t-test comparing mean ratio of strength measurement between the fractured and non-fractured leg for each treatment group between the 3 and 5 week time points.

In contrast, for animals treated with the β-TCP combined with either the low or high concentrations of rhPDGF-BB, there was a statistically significant increase in the ratio of the torsion strength at the 5 week time point as compared to the 3 week time point (Table 5). When the low and high concentration rhPDGF-BB treated animals were pooled, the time effect becomes even more significant with the ratio of torsion strength doubling from a value of 0.38 to 0.77, providing a highly significant p value, 0.0010. This data demonstrates that treatment with rhPDGF-BB led to a time dependent increase in the strength of the fracture site as compared to the two control groups evaluated in the study.

The data was further analyzed to evaluate direct torsion strength measurements between the fracture leg and the uninjured contralateral leg within each group and at both the 3 and 5 week time points. The data for the 3 week time points, presented in Table 6, demonstrates that for all four test groups, the biomechanical torsion strength measurement is statistically different between the fractured leg and the contralateral unfractured leg. Analysis of the 5 week time points (Table 7) showed that for the untreated group and the β-TCP matrix group, there was also a significant difference in the strength of the fractured and unfractured legs, similar to what was observed at the 3 week time point. In contrast, sufficient fracture repair had taken place for both the "low" and "high" rhPDGF-BB concentration groups, such that there was no longer a statistical difference in the strength of the fractured and unfractured legs.

TABLE 6

Comparing Injured Leg to Uninjured Leg at
3 Weeks for the Four Treatment Groups.

| Treatment Group | Injured Leg Mean Strength | Uninjured Leg Mean Strength | Two-Tailed P Value* |
|---|---|---|---|
| Untreated | 0.06 | 0.12 | 0.0333 |
| Control | 0.05 | 0.12 | 0.0035 |
| PDGF (Low Conc.) | 0.04 | 0.10 | 0.0003 |
| PDGF (High Conc.) | 0.05 | 0.12 | 0.0010 |

*P-Value results from a paired t-test comparing the mean strength values (Torque at Failure (Nm)) between the injured leg and the uninjured leg for each of the four treatment groups at the 3 week time point.

TABLE 7

Comparing Injured Leg to Uninjured Leg at
5 Weeks for the Four Treatment Groups.

| Treatment Group | Injured Leg Mean Strength | Uninjured Leg Mean Strength | Two-Tailed P-Value* |
|---|---|---|---|
| Untreated | 0.05 | 0.11 | 0.0179 |
| Control | 0.06 | 0.10 | 0.0378 |
| PDGF (Low Conc.) | 0.09 | 0.11 | 0.1649 |
| PDGF (High Conc.) | 0.08 | 0.11 | 0.1117 |

*P-value results from a paired West comparing the mean strength values (Torque at failure (Nm)) between the injured leg and the uninjured leg for each of the four treatment groups at the 5 week time point.

To evaluate a dose effect between the "low" and "high" rhPDGF-BB concentrations, the difference between the injured leg strength and the uninjured leg strength was determined for each PDGF test group for the 5 week time point. The data, presented in Table 8, demonstrates that there was no significant difference between the two groups, showing that there was no significant concentration effect between the "low" and "high" dosing regimes.

TABLE 8

Comparing PDGF Treatment Groups at 5 Weeks

| Frx + Low Mean Difference | Frx + High Mean Difference | Two-Tailed P-Value* |
|---|---|---|
| −0.028 | −0.026 | 0.9166 |

Note:
Analysis endpoint is difference between injured leg strength (Torque at Failure (Nm)) and uninjured leg strength. The difference was calculated for each individual animal within a test group, and then the mean value obtained, as presented in the table.
*P-Value results from a two-sample t-test.

As demonstrated by the results of the study, a composition comprising a PDGF solution disposed in a β-TCP/collagen matrix can enhance bone fracture repair. At the 5 week time point, the fractured legs of osteoporotic rats of the untreated and control groups as compared to the contralateral unfractured legs for each animal, were significantly weaker than the fractured legs of osteoporotic rats from the high and low concentration rhPDGF-BB groups as compared to the contralateral unfractured legs for each animal. Moreover, disposing "high" and "low" concentrations of PDGF solutions in a β-TCP/collagen matrix produced an increase in the ratio of strength of the fractured to unfractured contralateral legs at the 5 week time point as compared to the 3 week time point, thereby demonstrating a time dependent healing effect. In contrast, there was no observed increase in fracture strength between 3 and 5 week time points for the untreated and control groups. Additionally, the 0.3 mg/ml dose of rhPDGF-BB was at least as effective as the 1.0 mg/ml does of rhPDGF-BB when disposed in a β-TCP/collagen matrix for enhancing bone repair.

The biomechanical results of the study demonstrate that treatment with locally delivered PDGF results in a statistically significant time dependent increase in torsional strength at the fracture site to which the implant composition is applied. These findings are in contrast to the results obtained for two different control groups of animals to which the PDGF composition was not administered and in which no increase in fracture site strength was observed. These results demonstrate the efficacy of PDGF to enhance fracture repair in a relevant animal model, and confirm the benefit of using PDGF for stimulating fracture repair in a clinical setting.

The histologic and radiographic results also reveal that the administration of PDGF to treat impaired bone produces no untoward bone remodeling, no generation of ectopic bone formation, and no abnormal fibrotic response.

EXAMPLE 3

Healing of Long Bone Fractures

The PDGF compositions of the present invention are used to facilitate healing of long bone fractures and also in fractures of the ankle and hindfoot. Long bones to be treated include but are not limited to the humerus, ulna, radius, femur, tibia and fibula. While this example described the femur, it is to be understood that other long bones may be treated in a similar manner.

Some fractures of the femur are stabilized using insertion of intramedullary nails using techniques known to one of skill in the art of orthopedic surgery. The PDGF compositions of the present invention may be applied to the medullary canal before or during placement of the intramedullary nail. These PDGF compositions may be applied through a tube inserted into the medullary canal, and if the canal must be reamed to properly accept the intramedullary nail, the composition may be applied after reaming is complete and before insertion of the nail.

Alternatively, the intramedullary nail may be coated with the PDGF compositions of the present invention and then inserted into the canal. Alternatively, the PDGF compositions are applied to the holes drilled in bone to receive the screw.

The PDGF compositions of the present invention may also be applied to screws that traverse cortical bone near the femoral head and also to screws that traverse cortical bone at the distal femur to facilitate bone formation at these sites. Hardware such as nails and screws and other implements for performing this procedure are available commercially from suppliers such as Smith & Nephew, Memphis, Tenn.

EXAMPLE 4

Preparation of a Composition Comprising a Solution of PDGF and a Biocompatible Matrix A composition comprising a solution of PDGF and a biocompatible matrix was prepared according to the following procedure.

A pre-weighed block of biocompatible matrix comprising β-TCP particles was obtained. The β-TCP comprised pure β-TCP particles having an average diameter ranging from about 75 μm to about 300 μm. A β-TCP biocompatible matrix can be commercially obtained from Kensey Nash (Exton, Pa.).

A solution comprising rhPDGF-BB was obtained. rhPDGF-BB is commercially available from Chiron Corporation at a stock concentration of 10 mg/ml (i.e., Lot # QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson, New Brunswick, N.J.) and GEM 21S (BioMimetic Therapeutics, Franklin, Tenn.) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention, including 1.0 mg/ml.

A ratio of about 91 µl of rhPDGF-BB solution to about 100 mg dry weight of the β-TCP biocompatible matrix was used to produce the composition. The rhPDGF-BB solution was expelled on the biocompatible matrix with a syringe.

EXAMPLE 5

Method of Treating a Fracture of the Distal Radius
Experimental Design and Overview This multicenter study was performed to evaluate the handling characteristics and clinical utility (i.e. performance, radiographic parameters) of β-TCP+rhPDGF-BB for the treatment of unstable distal radius fractures that require an open reduction and external fixation (OREF) or internal fixation with a volar plate (ORIF).

Subjects who experienced a primary unstable fracture that was initially reduced under emergent conditions and loss of reduction were assessed for study enrollment. Each subject had a physical exam that incorporated a medical history and fracture etiology.

The subject's distal radius (DR) fracture was reduced intraoperatively and reclassified to determine if the fracture morphology was consistent with the preoperative fracture classification. If the intraoperative classification was different than the preoperative classification, this was noted on the intraoperative case report form (CRF). The subject was not enrolled into the study if the surgeon determined intraoperatively that the fracture did not meet the fracture enrollment criteria or the fracture could not be adequately reduced and stabilized according to the protocol.

The treatment groups of the study were as follows:

Group I (Experimental): OREF or ORIF (volar plate) with β-TCP+rhPDGF-BB (0.3 mg/ml) bone graft Group II (Control): OREF or ORIF (volar plate) without graft material Nineteen (19) subjects participated in the study with 10 placed in Group 1 and 9 placed in Group II. The average age of the subjects was 65 and all were women.

All subjects were immobilized postoperatively with a standard external fixator or volar plate, according to standard of care. The external fixator or the fiberglass cast was removed at the investigator's discretion based on the fracture healing assessment (recommended between 3 and 8 weeks post-operatively), and the date of removal of the immobilization was recorded. The subject was examined by the surgeon and certified hand therapist at 7-14 days, 3, 4, 5, and 9 weeks, and at 3 and 6 months for clinical, radiographic and computed tomography (CT; as required by protocol), and functional assessments, as well as complications and/or device related adverse events. The investigator may have requested the subjects to be evaluated for up to 24 months postoperatively to continue monitoring progress. Continuing follow-up was discussed with the subjects during the six month follow-up visit, and appropriate data was collected by the Investigator and reported to the Sponsor. All over-the-counter and prescribed medication usage was recorded. Each subject completed a Disability of the Arm, Shoulder and Hand (DASH) Quality of Life assessment that evaluates a subject's ability to perform both fine and gross motor functions in addition to other activities.

Clinical and functional assessments consisted of a hand assessment that involved a comparison of the subject's unaffected (normal) limb to the affected limb. Three consecutive grip strength measures were performed with a Jamar dynamometer, at the same grip setting (2nd rung recommended) and recorded. Range of motion (ROM) was measured consisting of pronation, supination, flexion and extension, and radial/ulnar deviation measured with a goniometer. The schedule for follow-up was noted in the Study Timeline Summary below (Table 10) and all sites attempted to keep the subject visits within the recommended visit windows. However, some subjects may not have been able to comply with all study visit windows due to scheduling conflicts related to the investigator's clinic days, physical therapy and/or radiology visits. The sponsor and/or investigator may have requested the subjects to be evaluated up to 24 months postoperatively, and the subjects were notified after their six month visit.

The surgeon performed radiographic assessments (as required by protocol) to monitor fracture healing. An independent radiographic and CT assessment was performed by a designated musculoskeletal radiologist(s) who assessed these radiographic parameters for healing. These fracture healing measurements were documented on the CRF and analyzed for fracture healing by an independent musculoskeletal radiologist according to the statistical analysis plan.

All postoperative complications and device-related adverse events were recorded on the appropriate CRF. If a subject required re-reduction or another surgical procedure for a serious adverse event or the device was removed, the subject continued to be monitored for safety until the end of the study. All subjects were monitored during the six-month trial and any subject who requesting study withdrawal or was withdrawn by the investigator was requested to provide a reason for study discontinuance.

TABLE 9

Study Timeline Summary

| Visit 1 Screening Visit ↓ Within 12 Days of Fracture | Visit 2 Surgical Visit ↓ Within 12 Days of Fracture Day 0 | Visit 3 Post Tx Follow Up ↓ Day 7-14 | Visit 4 Post Tx Follow Up ↓ Week 3 ± 3 days | Visit 5 Post Tx Follow Up ↓ Week 4 ± 3 days | Visit 6 Post Tx Follow Up ↓ Week 5 ± 3 days | Visit 7 Post Tx Follow Up ↓ Week 9 ± 7 days | Visit 8 Post Tx Follow Up ↓ Week 12 ± 14 days | Visit 9 Post Tx Follow Up ↓ Week 24 ± 14 days |
| --- | --- | --- | --- | --- | --- | --- | --- | --- |

The primary endpoint of the present study was grip strength measured as a percent relative to the contralateral arm. Secondary semi-quantitative radiographic endpoints included assessment of fracture healing including callus formation (primary and secondary), presence of fracture gaps between fragments, healing callus in peripheral cortex, healing callus bridging subchondral bone, presence of heterotopic bone formation, and an overall assessment of new bone fill within fracture gaps (% bone fill) Secondary quantitative measurements included axial radial shortening, radial angle, dorsal angle, distal radioulnar joint incongruity, and radiocarpal incongruity. Moreover, secondary clinical functional endpoints comprised time to removal of fiberglass cast, Semmes-Weinstein Monofilament Test, edema, pain, quality of life assessment (DASH), and range of motion including pronation, supination, flexion, extension, and radial/ulnar deviation.

Surgical Protocol: After subjects enrolled in the study, satisfying both the inclusion and exclusion criteria, the following surgical protocol was undertaken.

Open Reduction and External Fixation Standard PA, lateral, and oblique)(45°) plain radiographs of the affected and unaffected wrists were obtained prior to surgery. Fractures were classified using the AO and Frykman distal radius fracture systems. Plain PA and lateral radiographs of the opposite wrist were obtained prior to treatment.

Patients were brought into an operating room (OR) in the standard fashion to treat distal radius fractures with open reduction and external fixation after verification that all inclusion/exclusion criteria have been achieved.

All patients were given adequate preoperative anesthesia with either regional block or general anesthesia administered by the hand surgeon or plastic surgeon and/or anesthesiologist. All patients were given preoperative antibiotics intravenously according to standard procedures.

The affected limb was prepped and draped in the usual standard manner. The arm was exsanguinated of blood and tourniquet control was used for surgery. Standard OREF approach to the distal radius was accomplished. A dorsal small incision was made that allows access to the fracture site according to standard bone grafting procedures associated with external fixation.

The external fixator was placed according to standard procedures prior to reduction. The external fixator was locked in a suitable fracture position according to standard external fixation procedures.

Under direct visualization, fracture fragments were reduced either manually or with K-wires for joysticks. Provisional fixation was accomplished. Intraoperative radiographs were obtained to determine the adequacy of reduction (fluoroscans were acceptable). If adequate, a commercially available external fixator was placed using standard operative fixation procedures. If adequate reduction and stabilization was not obtained using an external fixator, additional pins (K-wires) were used to achieve adequate reduction. If the fracture was unable to be reduced with additional fixation instrumentation (such as plates) the patient was excluded from the study. In such cases, these subjects were defined as screen failures and not enrolled into the study, since the study device was not implanted.

Once the patient was verified to meet all study criteria, the randomization envelope was selected and the appropriate treatment documented and administered (Group I or Group II).

Reduction Verification: Intraoperative spot films were taken, at the discretion of the surgeon, to determine the adequacy of reduction. Attempts were made to reduce the fracture to original volar tilt (in relation to the contralateral side); however, restoration of the volar inclination to a neutral position was deemed acceptable. Evaluation of intraoperative films were restricted to assessment of the adequacy of reduction and were not viewed by the radiologist to determine quantitative or semi-quantitative outcomes.

Following fixation and reduction, the wound was irrigated prior to implantation and the β-TCP+rhPDGF-BB was mixed according to Example I and manually packed into the fracture space before final reduction or after reduction since there were spaces or voids following reduction and irrigation. For the purpose of this study, adequate fill was defined as filling the fracture space to extend to but not beyond the margins of the fracture and its defect.

The β-TCP+rhPDGF-BB graft material was implanted according to standard bone grafting procedures. The material was implanted prior to, during, or following reduction and external fixation at the investigator's discretion based on the stabilization technique associated with the fracture.

The graft was constructed to fill comminuted fracture spaces via interdigitation within comminuted cancellous bone, both dorsally, distally and proximally. The degree of fill required varied from less than 2 mm to as much as 2 cm depending on the amount of bone involved.

Care was taken to ensure that the hydrated graft particles did not migrate into articular spaces. Residual particles were carefully removed from surrounding soft tissue prior to closure. The surgical site was not irrigated following placement of the graft material.

Once the implant materials were mixed, the clinician waited 10 minutes prior to implantation. Sometimes, the mixed product was wet with the remaining rhPDGF-BB. A new sterile mixing device (spatula) was used for each mix. The investigator directed the assistant who performed the mixing to record the cumulative amount of implanted β-TCP containing PDGF, as well as the residual amount of β-TCP not implanted. The amount of β-TCP was calculated and documented using qualitative relative measurements (⅓, ⅔, All). The residual β-TCP was placed in a medicine cup to record the residual volume of β-TCP which was used to determine an accurate volume of β-TCP implanted.

After OREF and implantation of the graft material and wound closure was complete, postoperative AP, lateral, oblique and 30 degree articular surface view films of the fracture site were obtained prior to completing the surgery according to standard procedure.

Open Reduction and Internal Fixation with Volar Plate—Alternative Surgical Procedure:

Standard PA, lateral, and oblique (45°) plain radiographs of the affected and unaffected wrists were obtained prior to surgery. Fractures were classified using the AO distal radius fracture systems. Plain PA and lateral radiographs of the opposite wrist were also obtained prior to treatment.

Patients were brought into an operating room (OR) in to treat distal radius fractures with open reduction and internal fixation after verification that all inclusion/exclusion criteria were achieved.

All patients were given adequate preoperative anesthesia with either regional block or general anesthesia administered by the hand surgeon or plastic surgeon and/or anesthesiologist. All patients were given preoperative antibiotics intravenously according to standard procedures.

The affected limb was prepped and draped in the usual standard manner. The arm was exsanguinated of blood and tourniquet control was used for surgery. Standard anterior approach to the distal radius was accomplished. All flexor tendons and neurovascular structures, including the median nerve, were protected during the surgery. The flexor pollicis longus was retracted and/or elevated and the pronator teres muscle was detached from the anterior portion of the distal radius. Based on the amount of displacement and/or comminution, an extended distal radius fracture approach including release of the brachioradialis was employed.

Under direct visualization, fracture fragments were reduced either manually or with K-wires for joysticks. Provisional fixation was accomplished. Intraoperative radiographs were obtained to determine the adequacy of reduction (fluoroscans were acceptable). If adequate, a commercially available volar plate was placed using standard operative plating procedures. If adequate reduction and internal stabilization was unable to be obtained using a volar plate, additional pins (K-wires) were used to achieve adequate reduction. If the fracture was unable to be reduced with additional fixation instrumentation (such as dorsal plates) the patient was excluded from the study.

Once the patient was verified to meet all study criteria, the randomization envelope was selected and the appropriate treatment documented and administered (treatment or control).

Reduction Verification: Intraoperative spot films were taken, at the discretion of the surgeon, to determine the adequacy of reduction. Attempts were made to reduce the fracture to original volar tilt (in relation to the contralateral side); however, restoration of the volar inclination to a neutral position was deemed acceptable. Evaluation of intraoperative films was restricted to assessment of the adequacy of reduction and was not viewed by the radiologist to determine quantitative or semi-quantitative outcomes.

ORIF with volar plate+β-TCP/rhPDGF-BB: In Group I, the fracture was reduced and the volar plate was fixated in the identical manner as noted above. Following fixation, the wound was irrigated prior to implantation, and the β-TCP/rhPDGF-BB material was mixed according to Example I and manually packed into the fracture space before final reduction or after reduction since there were spaces or voids following reduction and irrigation. For the purpose of this study, adequate fill was defined as filling the fracture space to extend to but not beyond the margins of the fracture and its defect.

β-TCP/rhPDGF-BB graft material was implanted according to standard bone grafting procedures. The material was implanted prior to, during, or following reduction and internal fixation at the investigator's discretion based on the stabilization technique associated with the fracture.

The graft was mixed to fill comminuted fracture spaces via interdigitation within comminuted cancellous bone, both dorsally, distally and proximally. The volume of fill required varied from less than 2 mm to as much as 2 cm depending on the size of the bone void.

Care was taken to ensure that β-TCP/rhPDGF-BB graft material did not migrate into articular spaces. Residual graft material was carefully removed from surrounding soft tissue prior to closure. The surgical site was not irrigated following placement of the β-TCP/rhPDGF-BB graft material.

Once the implant materials were mixed, the clinician waited 10 minutes prior to implantation. Sometimes the mixed product was wet with the remaining rhPDGF-BB. A new sterile mixing device (spatula) was used for each mix. The investigator directed the assistant who performed the mixing to record the cumulative amount of implanted graft material, as well as the residual amount of graft material not implanted. The amount of graft material was calculated and documented using qualitative relative measurements (⅓, ⅔, All). The residual graft material was placed in a medicine cup to record the residual volume of graft material, which was used to determine an accurate volume of graft material implanted.

After ORIF and administration of the β-TCP/rhPDGF-BB material and wound closure was complete, postoperative AP, lateral, oblique and 30 degree articular surface view films of the fracture site were obtained prior to splinting according to standard procedure. Outcome data was collected from this study on findings derived from radiographs, CTs and from direct examination of extremity function. The frequency of these measurements is illustrated in Table 10.

TABLE 10

Frequency of Radiographic and Functional Assessments

| | | Radiographic Parameters | | | Functional Assessments | | | |
|---|---|---|---|---|---|---|---|---|
| | Event | Quantitative Radiographic Parameters | Semi-Quantitative Radiographic Parameters | Reduction Verification | Range of Motion | Grip Strength | Pain | DASH |
| Perioperative Fracture Management | Prior to Treatment | X | X | | | | | |
| | After Fracture Reduction | | | X | | | | |
| | During Implantation | | | X | | | | |
| | Post Reduction/ Implantation Prior to Fixation | | | X | | | | |
| | Immediately Post-Fixation | X | X | | | | | |
| Management of Injured Extremity | Day 7-14 | X | X | | X | X | X | X |
| | Week 3 | X | X | | X | X | X | X |
| | Week 4 | X | X | | X | X | X | X |
| | Week 5 | X | X | | X | X | X | X |
| | Week 9 | X± | X± | | X | X | X | X |

TABLE 10-continued

Frequency of Radiographic and Functional Assessments

| | Radiographic Parameters | | | Functional Assessments | | | |
|---|---|---|---|---|---|---|---|
| Event | Semi-Quantitative Radiographic Parameters | Quantitative Radiographic Parameters | Reduction Verification | Range of Motion | Grip Strength | Pain | DASH |
| Week 12 | X | X | | X | X | X | X |
| Week 24 | X | X | | X | X | X | X |

The results of the study indicated that treating distal radius fractures with compositions of the present invention comprising a PDGF solution disposed in a β-TCP matrix accelerated healing while leading to greater grip strengths by the 24$^{th}$ week of the study. Table 11 provides a comparison of grip strengths between subjects of Group I and Group II at various timepoints in the study.

TABLE 11

Grip Strength (% of Contralateral)

| Timepoint | Group I | Group II |
|---|---|---|
| Week 6 | 13 | 13 |
| Week 12 | 41 | 44 |
| Week 24 | 66 | 62 |

Moreover, Table 12 demonstrates a comparison of new bone fill within distal radius fracture gaps between subjects of Group I and Group II as a function of time.

TABLE 12

Assessment of New Bone Fill within Fracture Gaps

| | >50% New Bone Fill Within Fracture Gap | |
|---|---|---|
| Timepoint | Group I | Group II |
| Week 1 | 0/7 (0%) | 0/9 (0%) |
| Week 3 | 4/9 (44%) | 1/9 (11%) |
| Week 6 | 9/9 (100%) | 5/9 (56%) |
| Week 12 | 9/9 (100%) | 8/9 (89%) |
| Week 24 | 9/9 (100%) | 8/9 (89%) |

From the results provided in Table 12, each subject of Group I achieved greater than 50% new bone fill within the fracture gap of the distal radius in substantially less time than the subjects of Group II. The accelerated healing in subjects of Group I is encouraging for compromised patients, including the elderly, smokers, drinkers, diabetics, patients with poor circulation, and patients suffering from bone diseases such as osteoporosis.

Additionally, Table 13 provides a comparison of fractures clinically healed between Groups I and II.

TABLE 13

Assessment of Clinically Healed Fractures

| | Fractures Clinically Healed | |
|---|---|---|
| Timepoint | Group I | Group II |
| Week 6 | 9/10 (90%) | 9/9 (100%) |
| Week 12 | 9/10 (90%) | 8/9 (89%) |
| Week 24 | 10/10 (100%) | 9/9 (100%) |

As provided in Table 13, each fracture treated with a composition of the present invention was determined to be clinically healed.

The results of the study additionally indicated that application of compositions of the present invention to fractures of the distal radius did not result in ectopic bone formation or substantial inflammation of the surgical area.

EXAMPLE 6

Method of Inhibiting Secondary Vertebral Compression Fractures

Experimental Design and Overview

This prospective, randomized, controlled, single-center clinical trial is to evaluate the efficacy of compositions comprising a PDGF solution disposed in a tricalcium phosphate matrix for inhibiting secondary compression fractures in high risk vertebral bodies (HVBs) at the time of kyphoplasty of vertebral compression fractures. Comparisons are made between the control composition (β-tricalcium phosphate+sodium acetate buffer alone) and the experimental composition (β-tricalcium phosphate+rhPDGF-BB in sodium acetate). Therefore, the present study is a pilot, clinical trial to support the proof-or-principle of β-TCP+rh-PDGF-BB to prevent or decrease the likelihood of secondary vertebral compression fractures by increased bone formation in HVBs.

The study is performed on up to a total of 10 subjects requiring prophylactic treatment of HVBs at the time of kyphoplasty. Each subject receives the control and experimental formulations as defined above.

Potential subjects are screened to determine if they meet the inclusion and exclusion criteria If all entry criteria are achieved, the potential subjects are invited to participate in the clinical trial. All subjects considered for entry into the study are documented on the Screening Log and reasons for exclusion are recorded.

All subjects have undergone kyphoplasty and do not have a symptomatic VCF adjacent to the two vertebral bodies treated in this study. The subject is not to be enrolled into the study if the surgeon determines intraoperatively that the fracture does not meet the fracture enrollment criteria or other fractures exist that would preclude treatment in this protocol.

The treatment groups are:

Group I: Injectable β-TCP+sodium acetate buffer (control); and,

Group II: Injectable β-TCP+rhPDGF-BB (experimental)
- 0.1 mg/ml rhPDGF-BB (Subjects 1-5)
- 0.3 mg/ml rhPDGF-BB (Subjects 6-10)*
- 1.0 mg/ml rhPDGF-BB (Subjects 11-15)*

*Following completion of first post-operative follow-up visit with no adverse events attributable to the study device.

Both subject groups I and II are treated according to the standard protocols and follow-up for kyphoplasty/Vertebroplasty. The subject is examined by the surgeon at 7-14 days, and at 6, 12, 24, and 52 weeks for clinical, radiographic and quantitative computed tomography (QCT). All over-the-counter and prescribed medication usage is recorded. An independent radiologist, unaware of the patients' treatment group assignments, performs QCT analysis to assess bone density. These measurements are documented and analyzed.

All postoperative complications and device-related adverse events are recorded on the appropriate case report form. If a subject experiences a subsequent VCF during the study period or another surgical procedure for a serious adverse event or the investigational device is removed, the subject is monitored for safety until the end of the study. Those subjects who are re-operated and/or have the fracture fixation hardware removed are requested to give permission to examine the explants for histological purposes. All subjects are monitored during the 12-month trial and any subject who requests study withdrawal or is withdrawn by the investigator is requested to provide a reason for study discontinuance. Table 14 provides a timeline summary for the present study.

the time of surgery, the subject is considered a screen failure and not enrolled into the study.

Upon identification of the two HVBs, the investigator requests that the randomization code be opened to determine the study treatment administered. The randomization code specifies treatment with the experimental composition (Group II) either proximally or distally in relation to the level treated with kyphoplasty. The other HVB is treated with the control composition (Group I)

The experimental composition is mixed according to the procedure provided in Example 1. The concentration of rhPDGF-BB used is dependent upon the dose escalation scheme (subjects 01-05 are administered 0.15 mg/ml rhPDGF; subjects 06-10 are administered 0.3 mg/ml rhPDGF-BB, and subjects 11-15 are administered 1.0 mg/ml rhPDGF-BB)

Once mixed, the paste is loaded into a syringe for injection using aseptic technique. The syringes are clearly labeled with provided labels: "Experimental" or "Control". Once the experimental and control matrix materials are mixed, the clinician waits 10 minutes prior to implantation. A new sterile mixing device (spatula) is used for each mix. The investigator directs the assistant who performs the mixing to record the cumulative amount of implanted composition, as well as the residual amount of composition not implanted. The amount of composition is calculated and documented using qualitative relative measurements (⅓, ⅔, All).

An 8 to 16 gauge JAMSHIDI® available from Cardinal Health of Dublin, Ohio is inserted through an extrapedicular approach into the vertebral bodies requiring prophylactic treatment. The wire is passed through the JAMSHIDI® and the JAMSHIDI® through the stylet over the wire The appropriate mixed preparation is injected into the subject vertebral body. Care should be taken to minimize leakage of the paste outside of the vertebral body.

TABLE 14

Study Timeline Survey

| Visit 1 Screening Visit | Visit 2 Surgical Visit | Visit 3 Post Tx Follow Up | Visit 4 Post Tx Follow Up | Visit 5 Post Tx Follow Up | Visit 6 Post Tx Follow Up | Visit 7 Post Tx Follow Up |
|---|---|---|---|---|---|---|
| ↓ | ↓ | ↓ | ↓ | ↓ | ↓ | ↓ |
| Within 21 Days of Surgery | Within 21 Days of Screening | | | | | |
| | Day 0 | Day 7-14 | Week 6 ± 3 days | Week 12 ± 7 days | Week 24 ± 7 days | Week 52 ± 14 days |

The primary endpoint is the bone density at 12 weeks post-operatively measured by QCT scans. Secondary endpoints include subject pain and quality of life assessments.

Surgical Protocol: After subjects have been enrolled in the study, satisfying both the inclusion and exclusion criteria, the following surgical protocol is undertaken.

Patients are brought into an operating room (OR) in the standard fashion, and standard methods are used to perform the kyphoplasty procedure with methyl methacrylate cement augmentation of the fractured vertebral body. Standard radiographs are taken of the vertebral bodies treated with kyphoplasty and with preventative bone augmentation treatment.

Figure 6:
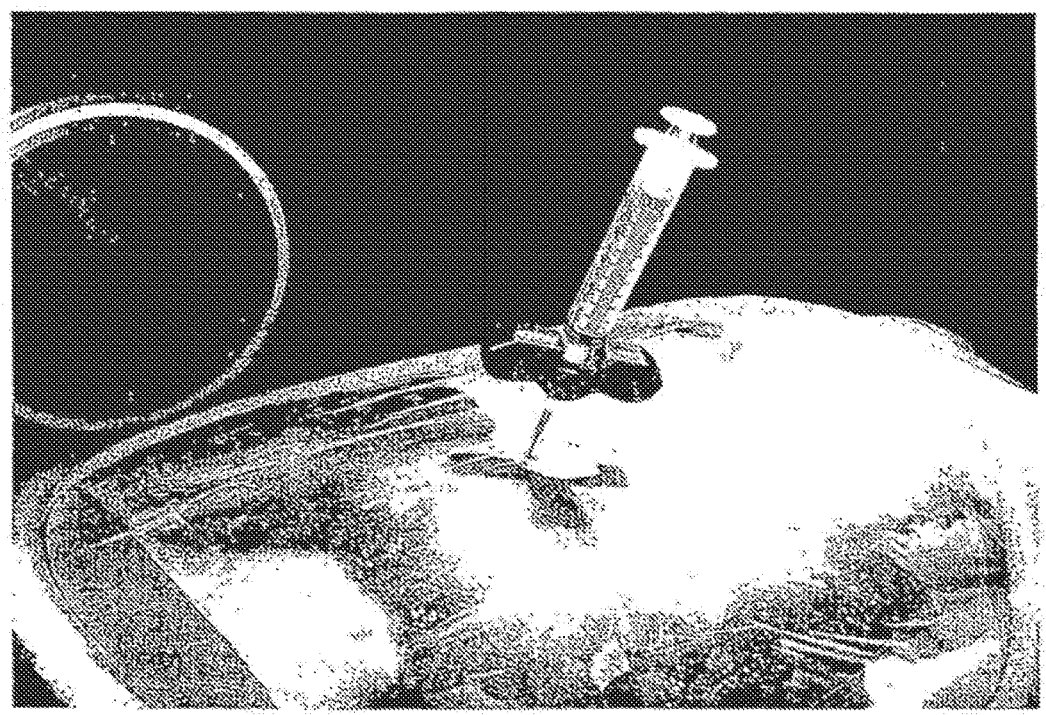
FIG. 6 illustrates a syringe and related apparatus penetrating tissue overlaying a vertebral body to deliver a composition of the present invention to the vertebral body according to an embodiment of the present invention.
Figure 7:
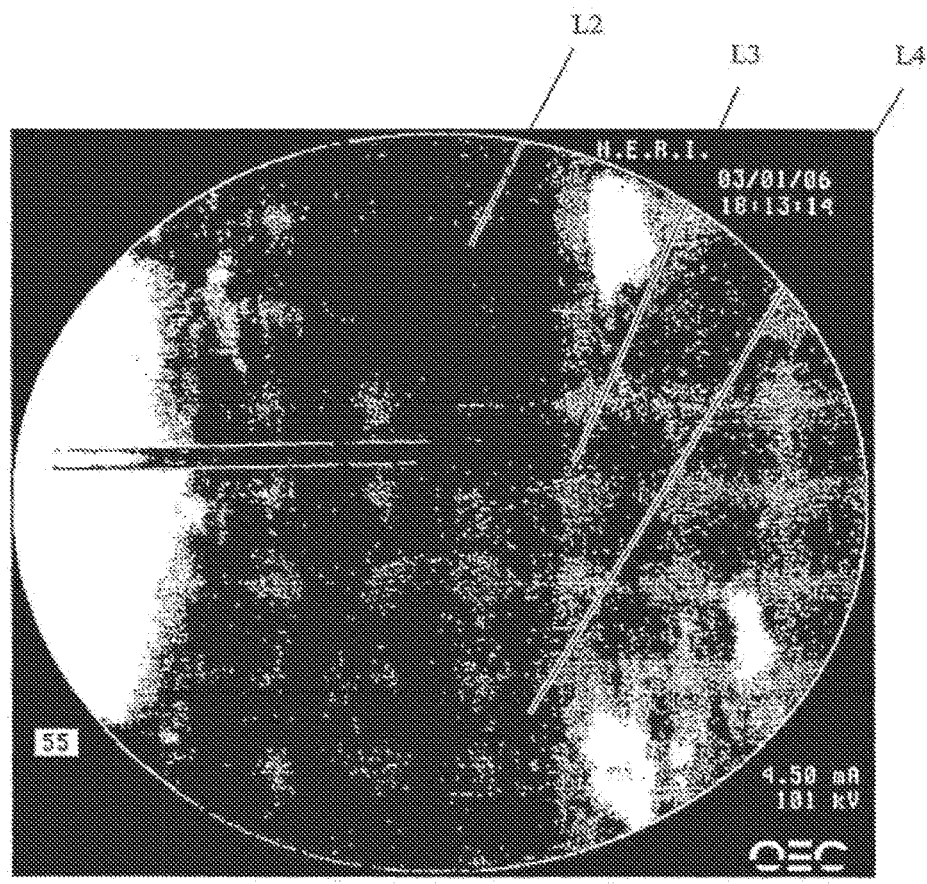
FIG. 7 is a radiograph illustrating injection of a composition into a vertebral body according to an embodiment of the present invention.

Following the kyphoplasty treatment, the investigator identifies and qualifies the two levels to be treated with prophylactic bone augmentation. If two (2) qualified vertebral bodies are not available for treatment, as determined at Contrast agents, according to embodiments of the present invention, can assist in identifying the leakage of the paste outside the vertebral body. FIG. 6 illustrates a syringe and related apparatus penetrating tissue overlaying a vertebral body to deliver a composition of the present invention to the vertebral body. FIG. 7 is a radiograph illustrating injection of a composition of the present invention into the vertebral body of the L3 vertebra according to one embodiment.

The instrumentation is removed. Thorough irrigation and standard wound closure techniques are employed.

Follow-up Evaluations: Subjects are seen for post-operative evaluations at days 7-14, and at 6 (±3 days), 12 (±7 days), 24 (±7 days), and 52 (±14 days) weeks post-surgery. Routine evaluations and procedures are performed during the follow-up period, as specified in the study flowchart of Table 15 below.

TABLE 15

Study Flow Chart and Follow-up Assessments

| Procedure | Screening Visit 1 | Surgery Visit 2 Day 0 | Visit 3 Day 7-14 | Visit 4 Week 6 ± 3 Days | Visit 5 Week 12 ± 7 Days | Visit 6 Week 24 ± 7 Days | Visit 7 Week 52 ± 14 Days |
|---|---|---|---|---|---|---|---|
| | | | | Post-Treatment Follow-up Evaluations | | | |
| Informed Consent | X[1] | | | | | | |
| Screening Log | X | | | | | | |
| Medical History | X | | | | | | |
| Physical Examination of Spine | X | X | X | X | X | X | X |
| Subject Eligibility Criteria Verification | X | X | | | | | |
| Identification of High-Risk Vertebral Bodies | X | | | | | | |
| Randomization | | X | | | | | |
| Kyphoplasty and Preventative Bone Augmentation | | X | | | | | |
| Volume of Graft Material Placed | | X | | | | | |
| Qualitative CT Assessments[2] | | X | | X | X | X | |
| Adverse Events/ Complications | | X | X | X | X | X | X |
| Concomitant Medications Review | X | X | X | X | X | X | X |

[1]Must occur prior to any study-specific procedures.
[2]Quantitative Computed Tomography (QCT) is performed according to standard protocol to obtain BMD data which is determined by the designated musculoskeletal radiologist.

Assessment of Effectiveness

Outcome data is collected from this study on findings derived from radiographs, QCTs, and from direct examination of function. The schedule of these measurements is provided in Table 16.

TABLE 16

Frequency of Radiographic and Functional Assessments

| | Study Parameters | | | |
|---|---|---|---|---|
| Timepoint | Plain film radiographs | Qualitative CT Scans | Pain | Function |
| Prior to Treatment | X | X | X | X |
| Immediately Post-Treatment | X | | | |
| Day 7-14 | | | X | |
| Week 6 | X | X | X | X |
| Week 12 | X | X | X | X |
| Week 24 | X | X | X | X |
| Week 52 | X | X | X | X |

Vertebral bodies injected with a composition comprising a PDGF solution disposed in a β-tricalcium phosphate matrix are expected to display increased bone mineral density (BMD).

Increased bone mineral density in a vertebral body can render the vertebral body less susceptible to fractures including secondary fractures induced by kyphoplasty/vertebroplasty operations.

EXAMPLE 7

Method of Inhibiting Vertebral Compression Fractures in Osteoporotic Individuals A method of inhibiting vertebral compression fractures in osteoporotic individuals comprises promoting bone formation in vertebral bodies through treatment with compositions comprising a PDGF solution disposed in a biocompatible matrix such as β-tricalcium phosphate.

Compositions of the present invention are mixed in accordance with that provided in Example 1. The concentration of PDGF in the PDGF solutions ranges from 0.3 mg/ml to 1.0 mg/ml. Once mixed, the composition is loaded into a syringe for injection using aseptic technique. The surgeon waits 10 minutes prior to implantation. A new sterile mixing device (spatula) is used for each mix.

The JAMSHIDI® is inserted through an extrapedicular approach into the vertebral bodies requiring prophylactic treatment. Vertebral bodies requiring prophylactic treatment, in some embodiments, comprise high risk vertebral bodies including vertebral bodies T5 through T12 and L1 through L4. The wire is passed through the Jamshidi and the Jamshidi through the stylet over the wire The appropriate mixed preparation is injected into the subject vertebral body. Care is taken to minimize leakage of the paste outside of the vertebral body. A plurality of vertebral bodies are treated according to the present example. Osteoporotic patients receiving this treatment have a lower incidence of vertebral compression fractures than untreated osteoporotic patients.

EXAMPLE 8

Evaluation of the Chronic Safety of rh-PDGF-BB Combined with Collagen/β-Tricalcium Phosphate Matrix in a Rabbit Paravertebral Implant Model Experimental Design and Overview: This study evaluated the safety of implanting injectable rhPDGF-BB/collagen/β-TCP material in a paravertebral intramuscular site adjacent to the spine of rabbits. The animals were observed for signs of neurotoxicity, and the implant sites with adjacent vertebral bodies and spinal cord were examined histologically to document tissue-specific responses to the material.

The study protocol and animal care was approved by the local IACUC and conducted according to AAALAC guidelines. Twelve (12) naïve, female, albino New Zealand rabbits weighing ≥2.5 kg were assigned to one of 4 groups: 0.3 mg/ml PDGF; 1.0 mg/ml PDGF; rubber; or acetate buffer. PDGF treated rabbits received 0.2 cc implants of appropriately concentrated rhPDGF-BB in matrix injected into a 1 cm pocket in the right paravertebral muscle adjacent to the L4-L5 vertebral bodies while high density polyethylene (HDPE) was implanted in a similar incision in the left paravertebral muscles near L2-L3 of the same animals. Rabbits in the sodium acetate buffer group received sodium acetate buffer in place of the PDGF+matrix implant, while those in the rubber group received only rubber in the right paravertebral muscle. One rabbit in each group was sacrificed at 30, 90, and 180 days post-surgery.

Body weights were measured prior to surgery and biweekly following surgery for the duration of the study. Radiographs were taken prior to surgery, immediately following surgery, and immediately prior to sacrifice. Digital photography of the surgical sites was performed during surgery and at the study end points. Weekly clinical observations of the implant sites were recorded for signs of erythema, edema, and inflammation and for signs of neurotoxicity, such as ambulatory changes. At necropsy, each implant site along with the adjacent vertebral body and spinal cord were harvested en bloc, fixed in formalin, and prepared for decalcified, paraffin embedded histopathological analysis.

Materials: The dosages of rhPDGF-BB tested in this study included 0.3 mg/ml and 1.0 mg/ml in 20 mM sodium acetate buffer, pH 6.0+/−0.5. The matrix material consisted of 20% lyophilized bovine type I collagen and 80% β-TCP with a particle size of 100-300 μm (Kensey Nash Corporation). Negative control material consisted of high-density polyethylene (HDPE and positive control material consisted of black rubber. Immediately prior to surgery, the rhPDGF-BB and control solutions were mixed with matrix material in a 3:1 liquid to mass ratio.

Briefly, the PDGF solution was allowed to saturate the material for 2 minutes then manually mixed to generate a paste-like consistency. The homogeneous distribution of rhPDGF-BB throughout the mixed material using this mixing technique was confirmed by eluting the PDGF from samples of similar mass and then quantifying the PDGF by ELISA (R&D Systems).

Results: Following manual mixing of 0.3 mg/ml rhPDGF-BB with the collagen/β-TCP matrix, the homogeneity of rhPDGF-BB throughout the mixed material was confirmed within +/−4% error across samples.

All animals recovered from surgery, and at the time of this writing, all clinical observations were reported to be normal with no signs of neurotoxicity or abnormal wound healing at the surgical sites. Two animals treated with sodium acetate buffer and matrix control exhibited minor scabbing at the surgical wounds which healed completely. One animal that received 0.3 mg/ml rhPDGF-BB exhibited slight erythema at the surgical site 3-4 days after surgery and then returned to normal appearance. A histopathological analysis of test article implant sites 29 days post-surgery indicated a mild amount of tissue in-growth into the implanted test materials and a mild inflammatory response. No ectopic or abnormal bone formation was observed in the vertebral bodies adjacent to the implant sites. These findings are summarized in Table 17 and compared with ratings for negative control HDPE implant sites.

TABLE 17

Summary of Histopathology Findings at Implant Sites 29 Days After Surgery

| [PDGF-BB] (mg/ml) | Macrophages | MGCs | Tissue In-growth | Ectopic Bone | Exostosis |
|---|---|---|---|---|---|
| 0.3 | 3, 1(NC) | 2, 0(NC) | 2, 0(NC) | 0, 0(NC) | 0, 0(NC) |
| 1.0 | 2, 2(NC) | 2, 0(NC) | 2, 0(NC) | 0, 0(NC) | 0, 0(NC) |

NC = Negative Control; MGC = multinucleated giant cells; Bioreactivity scale: 0 = Absent, 1 = Minimal/Slight, 2 = Mild, 3 = Moderate, 4 = Marked/Severe Preliminary evidence from this study based on clinical observations, suggests that collagen/β-tricalcium phosphate combined with either 1.0 mg/ml, 0.3 mg/ml rhPDGF-BB, or sodium acetate buffer does not elicit any acute or chronic neurotoxic effects. Histopathological assessment of the implant sites 29 days post-surgery indicated a normal and expected mild amount of tissue in-growth into the implanted material and a mild inflammatory response. No ectopic bone formation, exostosis, or abnormal bone resorption was observed at any of the implant sites. Based on observations of the animals treated in this study, collagen/β-tricalcium phosphate combined with either 1.0 mg/ml, 0.3 mg/ml rhPDGF-BB is safe to use when injected in close proximity to the spinal column.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A method of treating bone comprising applying a composition to the bone, wherein
    the composition comprises a solution comprising platelet-derived growth factor (PDGF) at a concentration in a range of 0.1 to 1.0 mg/mL in a buffer disposed in a biocompatible matrix;
    the biocompatible matrix is selected from the group consisting of i) particles of β-tricalcium phosphate having interconnected pores, and ii) particles β-tricalcium phosphate having interconnected pores and collagen;
    the β-tricalcium phosphate comprises pores and has a porosity greater than 50%;
    the particles of β-tricalcium phosphate have an average diameter ranging from 1 μm to 5 mm and,
    the bone is a fractured bone, an osteoporotic bone, a weakened bone, or a bone susceptible to damage due to increased compensatory load.

2. The method of claim 1, further comprising: applying the composition to orthopedic hardware; and, inserting the orthopedic hardware into the bone.

3. The method of claim 1, wherein the PDGF is PDGF-AA, PDGF-BB, PDGF-AB, PDGF-CC, or PDGF-DD, or a mixture thereof.

4. The method of claim 1, wherein the PDGF is rhPDGF-BB or a fragment thereof.

5. The method of claim 1, wherein the solution has a pH ranging from 3.0 to 8.0.

6. The method of claim 1, wherein the β-tricalcium phosphate has a calcium/phosphorous atomic ratio ranging from 0.5 to 2.0.

7. The method of claim 1, wherein the β-tricalcium phosphate comprises pores having diameters ranging from 1 μm to 1 mm.

8. The method of claim 1, wherein the β-tricalcium phosphate comprises particles having an average diameter ranging from 200 μm to 3000 μm.

9. The method of claim 1, wherein the particles of β-tricalcium phosphate have an average diameter in a range of 250 μm to 750 μm.

10. The method of claim 1, wherein the biocompatible matrix is the particles of β-tricalcium phosphate.

11. The method of claim 1, wherein the biocompatible is the particles of β-tricalcium phosphate and collagen.

12. The method of claim 11, wherein the collagen is present in an amount ranging from 15 weight percent to 35 weight percent of the biocompatible matrix.

13. The method of claim 12, wherein the composition is flowable.

14. The method of claim 1, wherein the biocompatible matrix comprises particles of β-tricalcium phosphate having a diameter ranging from 75 μm to 300 μm, and the biocompatible matrix further comprises 15 to 35% by weight of collagen.

15. The method of claim 14, wherein the PDGF has a concentration in a range of 0.25 to 0.5 mg/mL.

16. The method of claim 1, wherein the composition further comprises a contrast agent, one or more biologically active agents, or a mixture thereof.

17. The method of claim 1, wherein the bone is a humerus, ulna, radius, femur, tibia, fibula, patella, ankle bone, wrist bone, carpal, metacarpal, phalangeal, tarsal, metatarsal, rib, sternum, vertebra, scapula, clavicle, pelvis, or sacrum.

\* \* \* \* \*